US008124079B2

(12) United States Patent
Goetsch et al.

(10) Patent No.: US 8,124,079 B2
(45) Date of Patent: Feb. 28, 2012

(54) ANTI-IGF-IR ANTIBODIES AND USES THEREOF

(75) Inventors: Liliane Goetsch, Ayze (FR); Nathalie Corvaia, Collonges sous Salève (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 12/973,480

(22) Filed: Dec. 20, 2010

(65) Prior Publication Data

US 2011/0091479 A1   Apr. 21, 2011

Related U.S. Application Data

(62) Division of application No. 11/658,739, filed as application No. PCT/IB2005/002619 on Jul. 27, 2005, now Pat. No. 7,854,930.

(60) Provisional application No. 60/591,932, filed on Jul. 29, 2004.

(30) Foreign Application Priority Data

Jul. 29, 2004   (FR) ..................................... 04 08379

(51) Int. Cl.
*A61K 39/395* (2006.01)
*A61K 39/00* (2006.01)
*C12P 21/08* (2006.01)
*C07K 16/00* (2006.01)
*C07K 16/28* (2006.01)

(52) U.S. Cl. ............... 424/130.1; 424/133.1; 424/141.1; 424/142.1; 424/143.1; 435/70.21; 530/387.1; 530/387.3; 530/388.1; 530/388.15; 530/388.22

(58) Field of Classification Search ........................ None
See application file for complete search history.

(56) References Cited

U.S. PATENT DOCUMENTS

| 5,891,996 | A | 4/1999 | Mateo de Acosta del Rio et al. |
| 7,241,444 | B2 | 7/2007 | Goetsch et al. |
| 7,553,485 | B2 | 6/2009 | Goetsch et al. |
| 7,854,930 | B2 * | 12/2010 | Goetsch et al. ............ 424/130.1 |
| 2008/0063639 | A1 | 3/2008 | Goetsch et al. |
| 2008/0193445 | A1 | 8/2008 | Goetsch et al. |
| 2008/0286198 | A1 | 11/2008 | Goetsch et al. |
| 2009/0265797 | A1 | 10/2009 | Goetsch et al. |
| 2009/0324600 | A1 | 12/2009 | Haeuw et al. |

FOREIGN PATENT DOCUMENTS

| WO | 02/053596 A2 | 7/2002 |
| WO | 03/059951 A2 | 7/2003 |
| WO | 03/100008 A2 | 12/2003 |
| WO | 03/106621 A2 | 12/2003 |

OTHER PUBLICATIONS

Albanell et al., "Unraveling Resistance to Trastuzumab (Herceptin): Insulin-Like Growth Factor-I Receptor, a New Suspect," Journal of the National Cancer Institute, vol. 93, No. 24, Dec. 19, 2001, pp. 1830-1832.
Arteaga et al., "Growth Inhibition of Human Breast Cancer Cells in Vitro with an Antibody against the Type I Somatomedin Receptor," Cancer Research, vol. 49, Nov. 15, 1989, pp. 6237-6241.
Avruch, "Insulin signal transduction through protein kinase cascades," Molecular and Cellular Biochemistry, vol. 182, 1998, pp. 31-48.
Bailyes et al., "Insulin receptor/IGF-I receptor hybrids are widely distributed in mammalian tissues: quantification of individual receptor species by selective immunoprecipitation and immunoblotting," Biochem. J., vol. 327, 1997, pp. 209-215.
Baserga et al., "The IGF-I receptor in cell growth, transformation and apoptosis," Biochimica et Biophysica Acta, vol. 1332, 1997, pp. F105-F126.
Baserga, "The IGF-I Receptor in Cancer Research," Experimental Cell Research, vol. 253, 1999, pp. 1-6.
Bebbington et al., "High Level Expression of a Recombinant Antibody From Myeloma Cells Using a Glutamine Synthetase Gene as an Amplifiable Selectable Marker," Bio/Technology, vol. 10, Feb. 1992, pp. 169-175.
Belfiore et al., "Insulin/IGF-I hybrid receptors play a major role in IGF-I signaling in thyroid cancer," Biochimie, vol. 81, 1999, pp. 403-407.
Brechbiel et al., "Backbone-Substituted DTPA Ligands for 90Y Radioimmunotherapy," Bioconjugate Chem., vol. 2, 1991, pp. 187-194.
Burrow et al., "Expression of Insulin-Like Growth Factor Receptor, IGF-1, and IGF-2 in Primary and Metastatic Osteosarcoma," Journal of Surgical Oncology, vol. 69, 1998, pp. 21-27.
Carter, "Improving the Efficacy of Antibody-Based Cancer Therapies," Nature, vol. 1, Nov. 2001, pp. 118-129.
Cheatham et al., "Insulin Action and the Insulin Signaling Network," Endocrine Reviews, vol. 16, No. 2, Apr. 1995, pp. 117-142.
Christiansen et al., "A model for the quaternary structure of human placental insulin receptor deduced from electron microscopy," Proc. Natl. Acad. Sci. USA, vol. 88, Jan. 1991, pp. 249-252.
Ciardiello, "Epidermal Growth Factor Receptor Tyrosine Kinase Inhibitors as Anticancer Agents," Drugs, vol. 60, Suppl. 1, 2000, pp. 25-32.

(Continued)

*Primary Examiner* — Phuong Huynh
(74) *Attorney, Agent, or Firm* — Birch, Stewart, Kolasch & Birch, LLP.

(57) ABSTRACT

The present invention relates to novel antibodies capable of binding specifically to the human insulin-like growth factor I receptor IGF-IR and/or capable of specifically inhibiting the tyrosine kinase activity of said IGF-IR, especially monoclonal antibodies of murine, chimeric and humanized origin, as well as the amino acid and nucleic acid sequences coding for these antibodies. The invention likewise comprises the use of these antibodies as a medicament for the prophylactic and/or therapeutic treatment of cancers overexpressing IGF-IR or any pathology connected with the overexpression of said receptor as well as in processes or kits for diagnosis of illnesses connected with the overexpression of the IGF-IR. The invention finally comprises products and/or compositions comprising such antibodies in combination with anti-EGFR antibodies and/or anti-VEGF antibodies and/or antibodies directed against other growth factors involved in tumor progression or metastasis and/or compounds and/or anti-cancer agents or agents conjugated with toxins and their use for the prevention and/or the treatment of certain cancers.

8 Claims, 5 Drawing Sheets

OTHER PUBLICATIONS

Coppola et al., "A Functional Insulin-Like Growth Factor I Receptor is Required for the Mitogenic and Transforming Activities of the Epidermal Growth Factor Receptor," Molecular and Cellular Biology, vol. 14, No. 7, Jul. 1994, pp. 4588-4595.

De Meyts et al., "Mechanism of Insulin and IGF-I Receptor Activation and Signal Transduction Specificity," Annals of New York Academy of Sciences, 1995, pp. 388-401.

DeAngelis et al., "Insulin-Like Growth Factor I Receptor is Required for the Mitogenic and Transforming Activities of the Platelet-Derived Growth Factor Receptor," Journal of Cellular Physiology, vol. 164, 1995, pp. 214-221.

DeChiara et al., "A growth-deficiency phenotype in heterozygous mice carrying an insulin-like growth factor II gene disrupted by targeting," Nature, vol. 345, May 3, 1990, pp. 78-80.

Dupont et al., "Insulin and Insulin-Like Growth Factor I Receptors: Similarities and Differences in Signal Transduction," Hormone Research, vol. 55, Suppl. 2, 2001, pp. 22-26.

Frasca et al., "Insulin Receptor Isoform A, a Newly Recognized High-Affinity Insulin-Like Growth Factor II Receptor in Fetal and Cancer Cells," Molecular and Cellular Biology, vol. 19, No. 5, May 1999, pp. 3278-3288.

Gansow et al., "Chelates and antibodies: Current methods and new directions," Cancer Imaging with Radiolabeled Antibodies, Goldenberg (ed.), Kluwer Academic Publishers, 1990, pp. 153-171.

Gansow, "Newer Approaches to the Radiolabeling of Monoclonal Antibodies by Use of Metal Chelates," Nucl. Med. Biol., vol. 18, No. 4, 1991, pp. 369-381.

Grothey et al., "The role of insulin-like growth factor I and its receptor in cell growth, transformation, apoptosis, and chemoresistance in solid tumors," J. Cancer Res. Clin. Oncol., vol. 125, 1999, pp. 166-173.

Hakam et al., "Expression of Insulin-Like Growth Factor-I Receptor in Human Colorectal Cancer," Hum. Pathol., vol. 30, No. 10, Oct. 1999, pp. 1128-1133.

Happerfield et al., "The Localization of the Insulin-Like Growth Factor Receptor 1 (IGFR-1) in Benign and Malignant Breast Tissue," Journal of Pathology, vol. 183, 1997, pp. 412-417.

Herbst et al., "Epidermal Growth Factor Receptors as a Target for Cancer Treatment: The Emerging Role of IMC-C225 in the Treatment of Lung and Head and Neck Cancers," Seminars in Oncology, vol. 29, No. 1, Suppl. 4, Feb. 2002, pp. 27-36.

Hortobagyi, "Overview of Treatment Results with Trastuzumab (Herceptin) in Metastatic Breast Cancer," Seminars in Oncology, vol. 28, No. 6, Suppl. 18, Dec. 2001, pp. 43-47.

Jiang et al., "Induction of tumor suppression and glandular differentiation of A549 lung carcinoma cells by dominant-negative IGF-I receptor," Oncogene, vol. 18, 1999, pp. 6071-6077.

Jones et al., "Replacing the complementarity-determining regions in a human antibody with those from a mouse," Nature, vol. 321, May 29, 1986, pp. 522-525.

Kasuya et al., "Characterization of Human Placental Insulin-like Growth Factor-I/Insulin Hybrid Receptors by Protein Microsequencing and Purification," Biochemistry, vol. 32, 1993, pp. 13531-13536.

Kido et al., "The Insulin Receptor and Its Cellular Targets," The Journal of Clinical Endocrinology & Metabolism, vol. 86, No. 3, 2001, pp. 972-979.

Koehler et al., "Continuous cultures of fused cells secreting antibody of predefined specificity," Nature, vol. 256, Aug. 7, 1975, pp. 495-497.

Koval et al., "Interaction in vitro of the product of the c-Crk-II proto-oncogene with the insulin-like growth factor I receptor," Biochem. J., vol. 330, 1998, pp. 923-932.

Krejcarek et al., "Covalent Attachment of Chelating Groups to Macromolecules," Biochemical and Biophysical Research Communications, vol. 77, No. 2, 1977, pp. 581-585.

Laviola et al., "The Adapter Protein Grb10 Associates Preferentially with the Insulin Receptor as Compared with the IGF-I Receptor in Mouse Fibroblasts," J. Clin. Invest., vol. 99, No. 5, Mar. 1997, pp. 830-837.

Li et al., "Single-chain antibodies against human insulin-like growth factor I receptor: expression, purification, and effect on tumor growth," Cancer Immunol. Immunother., vol. 49, 2000, pp. 243-252, XP-001113064.

Li et al., "Two New Monoclonal Antibodies Against the Alpha Subunit of the Human Insulin-Like Growth Factor-I Receptor," Biochemical and Biophysical Research Communications, vol. 196, No. 1, Oct. 15, 1993, pp. 92-98.

Louvi et al., "Growth-Promoting Interaction of IGF-II with the Insulin Receptor during Mouse Embryonic Development," Developmental Biology, vol. 189, Article No. DB978666, 1997, pp. 33-48.

Lu et al., Insulin-Like Growth Factor-I Receptor Signaling and Resistance to Trastuzumab (Herceptin), Journal of the National Cancer Institute, vol. 93, No. 24, Dec. 19, 2001, pp. 1852-1857.

Meares et al., "Conjugation of Antibodies with Bifunctional Chelating Agents: Isothiocyanate and Bromoacetamide Reagents, Methods of Analysis, and Subsequent Addition of Metal Ions," Analytical Biochemistry, vol. 142, 1984, pp. 68-78.

Moller et al., "Tissue-Specific Expression of Two Alternatively Spliced Insulin Receptor mRNAs in Man," Molecular Endocrinology, vol. 3, 1989, pp. 1263-1269.

Morrione et al., "Failure of the Bovine Papillomavirus to Transform Mouse Embryo Fibroblasts with a Targeted Disruption of the Insulin-Like Growth Factor I Receptor Genes," Journal of Virology, vol. 69, No. 9, Sep. 1995, pp. 5300-5303.

Mosthaf et al., "Functionally distinct insulin receptors generated by tissue-specific alternative splicing," The EMBO Journal, vol. 9, No. 8, 1990, pp. 2409-2413.

Mountain et al., "Engineering Antibodies for Therapy," Biotechnology and Genetic Engineering Reviews, vol. 10, Dec. 1992, pp. 1-142.

Nakae et al., "Distinct and Overlapping Functions of Insulin and IGF-I Receptors," Endocrine Reviews, vol. 22, No. 6, 2001, pp. 818-835.

Needleman et al., "A General Method Applicable to the Search for Similarities in the Amino Acid Sequence of Two Proteins," J. Mol. Biol., vol. 48, 1970, pp. 443-453.

Pandini et al., "Insulin and Insulin-like Growth Factor-I (IGF-I) Receptor Overexpression in Breast Cancers Leads to Insulin/IGF-I Hybrid Receptor Overexpression: Evidence for a Second Mechanism of IGF-I Signaling," Clinical Cancer Research, vol. 5, Jul. 1999, pp. 1935-1944.

Pandini et al., "Insulin/Insulin-like Growth Factor I Hybrid Receptors Have Different Biological Characteristics Depending on the Insulin Receptor Isoform Involved," The Journal of Biological Chemistry, vol. 277, No. 42, Oct. 18, 2002, pp. 39684-39695.

Pearson et al., "Improved tools for biological sequence comparison," Proc. Natl. Acad. Sci. USA, vol. 85, Apr. 1988, pp. 2444-2448.

Phy et al., "Insulin and Messenger Ribonucleic Acid Expression of Insulin Receptor Isoforms in Ovarian Follicles from Nonhirsute Ovulatory Women and Polycystic Ovary Syndrome Patients," J. Clin. Endocrinol. Metab., vol. 89, No. 7, 2004, pp. 3561-3566.

Prisco et al., "Insulin and IGF-I Receptors Signaling in Protection from Apoptosis," Horm. Metab. Res., vol. 31, 1999, pp. 80-89.

Railo et al., "The Prognostic Value of Insulin-like Growth Factor-I in Breast Cancer Patients. Results of a Follow-up Study on 126 Patients," Eur. J. Cancer, vol. 30A, No. 3, 1994, pp. 307-311.

Riechmann et al., "Reshaping human antibodies for therapy," Nature, vol. 332, Mar. 24, 1988, pp. 323-327.

Rodeck et al., "Interactions Between Growth Factor Receptors and Corresponding Monoclonal Antibodies in Human Tumors," Journal of Cellular Biochemistry, vol. 35, 1987, pp. 315-320.

Roth et al., "Insulin and Insulin-like Growth Factor Receptors and Responses," Cold Spring Harbor Symposia on Quantitative Biology, vol. 53, 1988, pp. 537-543.

Salomon et al., "Epidermal growth factor-related peptides and their receptors in human malignancies," Critical Reviews in Oncology/Hematology, vol. 19, 1995, pp. 183-232.

Sasaoka et al., "Comparison of the Insulin and Insulin-Like Growth Factor 1 Mitogenic Intracellular Signaling Pathways," Endocrinology, vol. 137, No. 10, 1996, pp. 4427-4434.

Sciacca et al., "Insulin receptor activation by IGF-II in breast cancers: evidence for a new autocrine/paracrine mechanism," Oncogene, vol. 18, 1999, pp. 2471-2479.

Scotlandi et al., "Blockage of Insulin-like Growth Factor-I Receptor Inhibits the Growth of Ewing's Sarcoma in Athymic Mice," Cancer Research, vol. 58, Sep. 15, 1998, pp. 4127-4131.

Seely et al., "A Functional Assessment of Insulin/Insulin-Like Growth Factor-I Hybrid Receptors," Endocrinology, vol. 136, No. 4, 1995, pp. 1635-1641.

Sell et al., "Effect of a Null Mutation of the Insulin-Like Growth Factor I Receptor Gene on Growth and Transformation of Mouse Embryo Fibroblasts," Molecular and Cellular Biology, vol. 14, No. 6, Jun. 1994, pp. 3604-3612.

Sell et al., "Simian virus 40 large tumor antigen is unable to transform mouse embryonic fibroblasts lacking type 1 insulin-like growth factor receptor," Proc. Natl. Acad. Sci. USA, vol. 90, Dec. 1993, pp. 11217-11221.

Singer et al., "Optimal Humanization of 1B4, an Anti-CD18 Murine Monoclonal Antibody, is Achieved by Correct Choice of Human V-Region Framework Sequences," The Journal of Immunology, vol. 150, No. 7, Apr. 1, 1993, pp. 2844-2857.

Singh, "Insulin-like Growth Factor System in Growth, Development and Carcinogenesis," Journal of Clinical Ligand Assay, vol. 23, No. 3, Fall 2000, pp. 214-232.

Smith et al., "Comparison of Biosequences," Advances in Applied Mathematics, vol. 2, 1981, pp. 482-489.

Soos et al., "Receptors for insulin and insulin-like growth factor-I can form hybrid dimers," Biochem. J., vol. 270, 1990, pp. 383-390.

Tatusova et al., "BLAST 2 Sequences, a new tool for comparing protein and nucleotide sequences," FEMS Microbiology Letters, vol. 174, 1999, pp. 247-250.

Valentinis et al., "Growth and Differentiation Signals by the Insulin-like Growth Factor 1 Receptor in Hemopoietic Cells are Mediated through Different Pathways," The Journal of Biological Chemistry, vol. 274, No. 18, Apr. 30, 1999, pp. 12423-12430.

Vella et al., "The IGF system in thyroid cancer: new concepts," J. Clin. Pathol.: Mol. Pathol., vol. 54, 2001, pp. 121-125.

Verhoeyen et al., "Engineering of Antibodies," BioEssays, vol. 8, No. 2, Feb./Mar. 1988, pp. 74-78.

Verhoeyen et al., "Reshaping Human Antibodies: Grafting an Antilysozyme Activity," Science, vol. 239, 1988, pp. 1534-1536.

White, "The IRS-signalling system: A network of docking proteins that mediate insulin action," Mol. Cell. Biochem., vol. 182, 1998, pp. 3-11.

Wraight et al., "Reversal of epidermal hyperproliferation in psoriasis by insulin-like growth factor I receptor antisense oligonucleotides," Nature Biotechnology, vol. 18, May 2000, pp. 521-526.

Zia et al., "Monoclonal Antibody Alpha IR-3 Inhibits Non-Small Cell Lung Cancer Growth In Vitro and In Vivo," Journal of Cellular Biochemistry Supplement, vol. 24, 1996, pp. 269-275.

* cited by examiner

SEQUENCE LISTING

```
<160> NUMBER OF SEQ ID NOS: 26

<210> SEQ ID NO 1
<211> LENGTH: 16
<212> TYPE: PRT
<213> ORGANISM: Mus musculus

<400> SEQUENCE: 1

Arg Ser Ser Gln Thr Ile Ile His Ser Asn Gly Asn Thr Tyr Leu Glu
1               5                   10                  15

<210> SEQ ID NO 2
<211> LENGTH: 7
<212> TYPE: PRT
<213> ORGANISM: Mus musculus

<400> SEQUENCE: 2

Lys Val Ser Asn Arg Phe Ser
1               5

<210> SEQ ID NO 3
<211> LENGTH: 10
<212> TYPE: PRT
<213> ORGANISM: Mus musculus

<400> SEQUENCE: 3

Phe Gln Gly Ser His Val Pro Tyr Thr Phe
1               5                   10

<210> SEQ ID NO 4
<211> LENGTH: 5
<212> TYPE: PRT
<213> ORGANISM: Mus musculus
```

-continued

```
<400> SEQUENCE: 4

Asp Tyr Trp Met Asn
1               5

<210> SEQ ID NO 5
<211> LENGTH: 17
<212> TYPE: PRT
<213> ORGANISM: Mus musculus

<400> SEQUENCE: 5

Leu Ile His Pro Ser Asp Ser Glu Thr Arg Leu Asp Gln Asn Phe Tyr
1               5                   10                  15

Asp

<210> SEQ ID NO 6
<211> LENGTH: 13
<212> TYPE: PRT
<213> ORGANISM: Mus musculus

<400> SEQUENCE: 6

Ser Val Ile Tyr Tyr Gly Asn Tyr Arg Trp Tyr Phe Asp
1               5                   10

<210> SEQ ID NO 7
<211> LENGTH: 11
<212> TYPE: PRT
<213> ORGANISM: Mus musculus

<400> SEQUENCE: 7

Lys Ala Ser Gln Asn Val Val Thr Asn Val Ala
1               5                   10

<210> SEQ ID NO 8
<211> LENGTH: 7
<212> TYPE: PRT
<213> ORGANISM: Mus musculus

<400> SEQUENCE: 8

Ser Ala Ser Tyr Arg Tyr Ser
1               5

<210> SEQ ID NO 9
<211> LENGTH: 9
<212> TYPE: PRT
<213> ORGANISM: Mus musculus

<400> SEQUENCE: 9

His Gln Tyr Asn Asn Phe Pro Leu Thr
1               5

<210> SEQ ID NO 10
<211> LENGTH: 5
<212> TYPE: PRT
<213> ORGANISM: Mus musculus

<400> SEQUENCE: 10

Glu Tyr Gly Val Ser
1               5

<210> SEQ ID NO 11
<211> LENGTH: 16
<212> TYPE: PRT
<213> ORGANISM: Mus musculus

<400> SEQUENCE: 11
```

```
Val Ile Trp Gly Gly Arg Asp Thr Tyr Tyr His Ser Pro Leu Lys Ser
1               5                   10                  15

<210> SEQ ID NO 12
<211> LENGTH: 6
<212> TYPE: PRT
<213> ORGANISM: Mus musculus

<400> SEQUENCE: 12

His Glu Gly Met Asp Tyr
1               5

<210> SEQ ID NO 13
<211> LENGTH: 11
<212> TYPE: PRT
<213> ORGANISM: Mus musculus

<400> SEQUENCE: 13

Ile Thr Ser Thr Asp Ile Asp Asp Asp Met Asn
1               5                   10

<210> SEQ ID NO 14
<211> LENGTH: 7
<212> TYPE: PRT
<213> ORGANISM: Mus musculus

<400> SEQUENCE: 14

Glu Gly Asn Thr Leu Arg Pro
1               5

<210> SEQ ID NO 15
<211> LENGTH: 9
<212> TYPE: PRT
<213> ORGANISM: Mus musculus

<400> SEQUENCE: 15

Leu Gln Ser Asp Lys Met Pro Leu Thr
1               5

<210> SEQ ID NO 16
<211> LENGTH: 5
<212> TYPE: PRT
<213> ORGANISM: Mus musculus

<400> SEQUENCE: 16

Asn Tyr Ala Met Ser
1               5

<210> SEQ ID NO 17
<211> LENGTH: 16
<212> TYPE: PRT
<213> ORGANISM: Mus musculus

<400> SEQUENCE: 17

Ser Ile Gly Ser Ala Gly Tyr Ile His Tyr Pro Asp Ser Val Lys Gly
1               5                   10                  15

<210> SEQ ID NO 18
<211> LENGTH: 9
<212> TYPE: PRT
<213> ORGANISM: Mus musculus

<400> SEQUENCE: 18

Glu Gly Gly Leu Val Trp Phe Ala Tyr
1               5
```

<210> SEQ ID NO 19
<211> LENGTH: 112
<212> TYPE: PRT
<213> ORGANISM: Mus musculus

<400> SEQUENCE: 19

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Ile His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 20
<211> LENGTH: 123
<212> TYPE: PRT
<213> ORGANISM: Mus musculus

<400> SEQUENCE: 20

Gln Ala Gln Leu Gln Gln Pro Gly Ala Val Leu Val Arg Pro Gly Ala
1               5                   10                  15

Ser Val Lys Leu Ser Cys Lys Ala Ser Ser Tyr Ser Phe Thr Asp Tyr
            20                  25                  30

Trp Met Asn Trp Val Lys Arg Pro Gly Gln Gly Leu Gln Trp Ile
        35                  40                  45

Gly Leu Ile His Pro Ser Asp Ser Glu Thr Arg Leu Asp Gln Asn Phe
    50                  55                  60

Lys Asp Lys Ala Thr Leu Thr Val Asp Lys Phe Ser Ser Thr Ala Tyr
65                  70                  75                  80

Met Gln Leu Asn Ser Pro Thr Ser Glu Asp Ser Ala Val Tyr Tyr Cys
                85                  90                  95

Thr Arg Ser Val Ile Tyr Tyr Gly Asn Tyr Arg Trp Tyr Phe Asp Val
            100                 105                 110

Trp Gly Ala Gly Thr Thr Val Thr Val Ser Ser
        115                 120

<210> SEQ ID NO 21
<211> LENGTH: 107
<212> TYPE: PRT
<213> ORGANISM: Mus musculus

<400> SEQUENCE: 21

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Thr Asn
            20                  25                  30

Val Ala Trp Tyr Gln His Lys Pro Gly His Ser Pro Lys Pro Leu Ile
        35                  40                  45

Tyr Ser Ala Ser Tyr Arg Tyr Ser Gly Val Pro Asp Arg Phe Thr Gly

```
                    50                  55                  60
Ser Gly Ser Gly Thr Asp Phe Thr Leu Thr Ile Asn Asn Val Gln Ser
 65                  70                  75                  80

Glu Asp Leu Ala Glu Tyr Phe Cys His Gln Tyr Asn Asn Phe Pro Leu
                     85                  90                  95

Thr Phe Gly Ala Gly Thr Lys Leu Glu Leu Lys
                    100                 105

<210> SEQ ID NO 22
<211> LENGTH: 114
<212> TYPE: PRT
<213> ORGANISM: Mus musculus

<400> SEQUENCE: 22

Gln Val Gln Leu Lys Glu Ser Gly Pro Gly Leu Val Ala Pro Ser Gln
  1               5                  10                  15

Ser Leu Ser Ile Thr Cys Thr Val Ser Gly Phe Ser Leu Asn Glu Tyr
                 20                  25                  30

Gly Val Ser Trp Ile Arg Gln Pro Pro Gly Lys Gly Leu Glu Trp Leu
             35                  40                  45

Gly Val Ile Trp Gly Gly Arg Asp Thr Tyr Tyr His Ser Pro Leu Lys
         50                  55                  60

Ser Arg Leu Ser Ile Thr Lys Asp Asn Ser Lys Ser Gln Val Phe Leu
 65                  70                  75                  80

Lys Met Asn Ser Leu Gln Thr Asp Asp Thr Ala Met Tyr Tyr Cys Ala
                 85                  90                  95

Lys His Glu Gly Met Asp Tyr Trp Gly Gln Gly Thr Ser Val Thr Val
                100                 105                 110

Ser Ser

<210> SEQ ID NO 23
<211> LENGTH: 114
<212> TYPE: PRT
<213> ORGANISM: Mus musculus

<400> SEQUENCE: 23

Gln Val Gln Leu Lys Glu Ser Gly Pro Gly Leu Val Ala Pro Ser Gln
  1               5                  10                  15

Ser Leu Ser Ile Thr Cys Thr Val Ser Gly Phe Ser Leu Asn Glu Tyr
                 20                  25                  30

Gly Val Ser Trp Ile Arg Gln Pro Pro Gly Lys Gly Leu Glu Trp Leu
             35                  40                  45

Gly Val Ile Trp Gly Gly Gly Asp Thr Tyr Tyr His Ser Pro Leu Lys
         50                  55                  60

Ser Arg Leu Ser Ile Thr Lys Asp Asn Ser Lys Ser Gln Val Phe Leu
 65                  70                  75                  80

Lys Met Asn Ser Leu Gln Thr Asp Asp Thr Ala Met Tyr Tyr Cys Ala
                 85                  90                  95

Lys His Glu Gly Met Asp Tyr Trp Gly Gln Gly Thr Ser Val Thr Val
                100                 105                 110

Ser Ser

<210> SEQ ID NO 24
<211> LENGTH: 107
<212> TYPE: PRT
<213> ORGANISM: Mus musculus

<400> SEQUENCE: 24
```

```
Glu Thr Thr Val Thr Gln Ser Pro Ala Ser Leu Ser Val Ala Thr Gly
1               5                   10                  15

Glu Lys Val Thr Ile Arg Cys Ile Thr Ser Thr Asp Ile Asp Asp Asp
                20              25              30

Met Asn Trp Tyr Gln Gln Lys Pro Gly Glu Pro Pro Lys Leu Leu Ile
            35              40              45

Ser Glu Gly Asn Thr Leu Arg Pro Gly Val Pro Ser Arg Phe Ser Ser
    50              55              60

Ser Gly Tyr Gly Thr Asp Phe Val Leu Thr Ile Glu Asn Thr Leu Ser
65              70              75              80

Glu Asp Val Ala Asp Tyr Tyr Cys Leu Gln Ser Asp Lys Met Pro Leu
                85              90              95

Thr Phe Gly Ala Gly Thr Lys Leu Glu Leu Lys
            100             105

<210> SEQ ID NO 25
<211> LENGTH: 117
<212> TYPE: PRT
<213> ORGANISM: Mus musculus

<400> SEQUENCE: 25

Glu Val Asn Leu Val Glu Ser Gly Gly Ile Leu Val Lys Pro Gly Gly
1               5                   10                  15

Ser Leu Arg Leu Ser Cys Ala Ala Ser Gly Phe Thr Phe Ser Asn Tyr
                20              25              30

Ala Met Ser Trp Val Arg Gln Thr Pro Glu Lys Arg Leu Glu Trp Val
            35              40              45

Ala Ser Ile Gly Ser Ala Gly Tyr Ile His Tyr Pro Asp Ser Val Lys
    50              55              60

Gly Arg Phe Thr Ile Ser Arg Asp Asn Ala Arg Asn Ile Leu Tyr Leu
65              70              75              80

Gln Met Ser Ser Leu Arg Ser Glu Asp Thr Ala Met Tyr Tyr Cys Ala
                85              90              95

Arg Glu Gly Gly Leu Val Trp Phe Ala Tyr Trp Gly Gln Gly Thr Leu
            100             105             110

Val Thr Val Ser Ala
        115

<210> SEQ ID NO 26
<211> LENGTH: 16
<212> TYPE: PRT
<213> ORGANISM: Mus musculus

<400> SEQUENCE: 26

Val Ile Trp Gly Gly Asp Thr Tyr Tyr His Ser Pro Leu Lys Ser
1               5                   10                  15
```

ANTI-IGF-IR ANTIBODIES AND USES THEREOF

CROSS REFERENCE TO RELATED APPLICATIONS

This application is a Divisional of Application No. 11/658,739 filed on Jan. 29, 2007, now U.S. Pat. No. 7,854,930, which issued Dec. 21, 2010, and which is a National Phase of PCT International Application No. PCT/IB2005/002619 filed on Jul. 27, 2005, which claims the benefit of U.S. Provisional Application No. 60/591,932 filed on Jul. 29, 2004, and to patent application Ser. No. 0408379 filed in France, on Jul. 29, 2004. The entire contents of all of the above applications are hereby incorporated by reference.

BACKGROUND OF THE INVENTION

The present invention relates to novel antibodies capable of binding specifically to the human insulin-like growth factor I receptor IGF-IR and/or capable of specifically inhibiting the tyrosine kinase activity of said IGF-IR, especially monoclonal antibodies of murine, chimeric and humanized origin, as well as the amino acid and nucleic acid sequences coding for these antibodies. The invention likewise comprises the use of these antibodies as a medicament for the prophylactic and/or therapeutic treatment of cancers overexpressing IGF-IR or any pathology connected with the overexpression of said receptor as well as in processes or kits for diagnosis of illnesses connected with the overexpression of the IGF-IR. The invention finally comprises products and/or compositions comprising such antibodies in combination with anti-EGFR antibodies and/or anti-VEGF antibodies and/or antibodies directed against other growth factors involved in tumor progression or metastasis and/or compounds and/or anti-cancer agents or agents conjugated with toxins and their use for the prevention and/or the treatment of certain cancers.

The insulin-like growth factor I receptor called IGF-IR is a well described receptor with tyrosine kinase activity having 70% homology with the insulin receptor IR. IGF-IR is a glycoprotein of molecular weight approximately 350,000.

It is a hetero-tetrameric receptor of which each half-linked by disulfide bridges is composed of an extracellular α-subunit and of a transmembrane β-subunit. IGF-IR binds IGF1 and IGF2 with a very high affinity (Kd #1 nM) but is equally capable of binding to insulin with an affinity 100 to 1000 times less. Conversely, the IR binds insulin with a very high affinity although the IGFs only bind to the insulin receptor with a 100 times lower affinity. The tyrosine kinase domain of IGF-IR and of IR has a very high sequence homology although the zones of weaker homology respectively concern the cysteine-rich region situated on the α-subunit and the C-terminal part of the β-subunit. The sequence differences observed in the α-subunit are situated in the binding zone of the ligands and are therefore at the origin of the relative affinities of IGF-IR and of IR for the IGFs and insulin respectively. The differences in the C-terminal part of the β-subunit result in a divergence in the signalling pathways of the two receptors; IGF-IR mediating mitogenic, differentiation and anti-apoptosis effects, while the activation of the IR principally involves effects at the level of the metabolic pathways (Baserga et al., Biochim. Biophys. Acta, 1332:F105-126, 1997; Baserga R., Exp. Cell. Res., 253:1-6, 1999).

The cytoplasmic tyrosine kinase proteins are activated by the binding of the ligand to the extracellular domain of the receptor. The activation of the kinases in its turn involves the stimulation of different intra-cellular substrates, including IRS-1, IRS-2, Shc and Grb 10 (Peruzzi F. et al., J. Cancer Res. Clin. Oncol., 125:166-173, 1999). The two major substrates of IGF-IR are IRS and She which mediate, by the activation of numerous effectors downstream, the majority of the growth and differentiation effects connected with the attachment of the IGFs to this receptor. The availability of substrates can consequently dictate the final biological effect connected with the activation of the IGF-IR. When IRS-1 predominates, the cells tend to proliferate and to transform. When Shc dominates, the cells tend to differentiate (Valentinis B. et al., J. Biol. Chem. 274:12423-12430, 1999). It seems that the route principally involved for the effects of protection against apoptosis is the phosphatidyl-inositol 3-kinases (PI 3-kinases) route (Prisco M. et al., Horm. Metab. Res., 31:80-89, 1999; Peruzzi F. et al., J. Cancer Res. Clin. Oncol., 125:166-173, 1999).

The role of the IGF system in carcinogenesis has become the subject of intensive research in the last ten years. This interest followed the discovery of the fact that in addition to its mitogenic and antiapoptosis properties, IGF-IR seems to be required for the establishment and the maintenance of a transformed phenotype. In fact, it has been well established that an overexpression or a constitutive activation of IGF-IR leads, in a great variety of cells, to a growth of the cells independent of the support in media devoid of fetal calf serum, and to the formation of tumors in nude mice. This in itself is not a unique property since a great variety of products of overexpressed genes can transform cells, including a good number of receptors of growth factors. However, the crucial discovery which has clearly demonstrated the major role played by IGF-IR in the transformation has been the demonstration that the R-cells, in which the gene coding for IGF-IR has been inactivated, are totally refractory to transformation by different agents which are usually capable of transforming the cells, such as the E5 protein of bovine papilloma virus, an overexpression of EGFR or of PDGRR, the T antigen of SV 40, activated ras or the combination of these two last factors (Sell C. et al., Proc. Natl. Acad. Sci., USA, 90:11217-11221, 1993; Sell C, et at, Mol. Cell. Biol., 14:3604-3612, 1994; Morrione A. J., Virol., 69:5300-5303, 1995; Coppola D. et al., Mol. Cell. Biol., 14:4588-4595, 1994; DeAngelis T. et at, J. Cell. Physiol., 164:214-221, 1995).

IGF-IR is expressed in a great variety of tumors and of tumor lines and the IGFs amplify the tumor growth via their attachment to IGF-IR. Other arguments in favor of the role of IGF-IR in carcinogenesis come from studies using murine monoclonal antibodies directed against the receptor or using negative dominants of IGF-IR. In effect, murine monoclonal antibodies directed against IGF-IR inhibit the proliferation of numerous cell lines in culture and the growth of tumor cells in vivo (Arteaga C. et at, Cancer Res., 49:6237-6241, 1989; Li et al., Biochem. Biophys. Res. Corn., 196:92-98, 1993; Zia F. et al., J. Cell. Biol., 24:269-275, 1996; Scotlandi K. et at, Cancer Res., 58:4127-4131,1998). It has likewise been shown in the works of Jiang et al. (Oncogene, 18:6071-6077, 1999) that a negative dominant of IGF-IR is capable of inhibiting tumor proliferation.

Cancer pathologies are characterized by an uncontrolled cellular growth. In several cancer, growth factors are specifically binding with their receptors and then transmit growth, transformation and/or survival signals to the tumoral cell. The growth factor receptors over-expression at the tumoral cell surface is largely described (Salomon D.S. et at, Crit. Rev. Oncol. Hematol., 1995, 19:183; Burrow S. et al., Surg. Oncol., 1998, 69:21; Hakam A. et al., Hum. Pathol., 1999, 30:1128; Railo M. J. et al., Bur. J. Cancer, 1994, 30:307; Happerfield L. C. et al., J. Pathol., 1997, 183:412). This over-expression, or abnormal activation, leading to a direct perturbation of cellular growth regulation mechanisms, can also affect the cell sensibility to induced apoptose by classical chemotherapies or radiotherapies.

During last few years, it has been shown that the targeting of growth factor receptors, like EGFR or Her2/neu over-expressed on the tumoral cell surface, with respectively humanized (herceptin®) or chimeric (C225) antibodies results in an significant inhibition of the tumoral growth in patients and in a significant increase of the efficacity of classical chemotherapy treatments (Carter P., Nature Rev. Cancer, 2001, 1(2):118; Hortobagyi G. N., Semin. Oncol., 2001, 28:43; Herbst R. S. et al., Semin. Oncol., 2002, 29:27). Other receptors like IGF-IR or VEGF-R (for vascular endothelial growth factor receptor) have been identified as potential target in several preclinical studies.

More particularly, IGF-IR is part of the tyrosine kinase receptors. It shows a high homology with the Insulin receptor (IR) which exist under two isoforms A and B.

Sequences of IR, isoforms A and B, are registered under Accession Numbers X02160. and M10051, respectively, in the NCBI Genbank. Other data, without limitations, relating to IR are incorporated herein by references (Vinten et al., 1991, Proc. Nati. Acad. Sci. USA, 88:249-252; Belfiore et al., 2002, The Journal of Biological Chemistry, 277:39684-39695; Durnesic et al., 2004, The Journal of Endocrinology & Metabolism, 89(7):3561-3566).

The IGF-IR and IR are tetrameric glycoproteins composed of two extracellular α- and two transmembrane β-subunits linked by disulfide bonds. Each α-subunit, containing the ligand-binding site is approximately 130- to 135-kDa, whereas each β-subunit containing the tyrosine kinase domain is approximately 90- to 95-kDa. These receptors share more than 50% overall amino acid sequence similarity and 84% similarity in the tyrosine kinase domain. After ligand binding, phosphorylated receptors recruit and phosphorylate docking proteins, including the insulin receptor substrate-1 protein family (IRS1), Gab1 and Shc (Avruch, 1998, Mol. Cell. Biochem., 182, 31-48; Roth et al., 1988, Cold Spring Harbor Symp. Quant. Biol. 53, 537-543; White, 1998, Mol. Cell. Biochem., 182, 3-11; Laviola et al., 1997, J. Clan. Invest. 99, 830-837; Cheatham et al., 1995, Endocr. Rev. 16, 117-142), leading to the activation of different intracellular mediators. Although both the IR and IGF-IR similarly activate major signalling pathways, differences exist in the recruitment of certain docking proteins and intracellular mediators between both receptors (Sasaoka et al., 1996, Endocrinology 137, 4427-4434; Nakae et al., 2001, Endocr. Rev. 22, 818-835; Dupont and Le Roith 2001, Horm. Res. 55, Suppl. 2, 22-26; Koval et al., 1998, Biochem. 3. 330, 923-932). These differences are the basis for the predominant metabolic effects elicited by IR activation and the predominant mitogenic, transforming and anti-apoptotic effects elicited by IGF-IR activation (De Meyts et al., 1995, Ann. N.Y. Acad. Sei., 766, 388-401; Singh et al., 2000, Prisco et al., 1999, Horm. Metab. Res. 31, 80-89; Kido et al. 2001, J. Clin. Endocrinol. Metab., 86, 972-979). Insulin binds with high affinity to the IR (100-fold higher than to the IGF-IR), whereas insulin-like growth factors (IGF1 and IGF2) bind to the IGF-IR with 100-fold higher affinity than to the IR.

The human IR exists in two isoforms, IR-A and IR-B, generated by alternative splicing of the IR gene that either excludes or includes 12 amino acid residues encoded by a small exon (exon 11) at the carboxy-terminus of the IR α-subunit. The relative abundance of IR isoforms is regulated by tissue specific and unknown factors (Moller et al., 1989, Mol. Endocrinol., 3, 1263-1269; Mosthaf et al., 1990, EMBO J., 9, 2409-2413). IR-B is the predominant a isoform in normal adult tissues (adipose tissue, liver and muscle) that are major target tissues for the metabolic effects of insulin (Moller et al., 1989; Mosthaf et al., 1990). IR-A is the predominant isoform in fetal tissues and mediates fetal growth in response to IGF2 (Frasca et al., 1999, Mol. Cell. Biol., 19, 3278-3288), as also suggested by genetic studies carried out in transgenic mice (DeChiara et al., 1990, Nature 345, 78-80; Louvi et al., 1997, Dev. Biol. 189, 33-48). Moreover, when cells transform and become malignant, dedifferentiation is often associated with an increased IR-A relative abundance (Pandini et al., 2002, The Journal of Biological Chemistry, Vol. 277, N° 42, pp39684-39695).

Given the high degree of homology, the insulin and IGF-I half-receptors (composed of one α- and one β-subunit) can heterodimerize, leading to the formation of insulin/IGF-I hybrid receptors (Hybrid-R) (Soos et al., 1990, Biochem J., 270, 383-390; Kasuya et al., 1993, Biochemistry 32, 13531-13536; Seely et al., 1995, Endocrinology 136, 1635-1641; Bailyes et al., 1997, Biochem J. 327, 209-215).

Both IR isoforms are equally able to form hybrids with IGF-IR. Hybrid-R, however, have different functional characteristics. Hybrid-RsB has reduced affinity for IGF1 and especially for IGF2. In contrast, Hybrid-RsA has a high affinity for IGF1 and bind also IGF2 and insulin at a physiological concentration range. The expression of Hybrid-RsA up-regulates the IGF system by two different mechanisms i) binding (with high affinity) and activation by both IGF1 and IGF2 (which do not occur with the Hybrid-RsB), activation of the IGF-IR pathway after insulin binding. Insulin binding to Hybrid-RsA phosphorylates the IGF-IR β-subunit and activates an IGF-IR-specific substrate (CrkII) so that Hybrid-RsA shifts insulin to IGF-IR signaling (Pandini et al., 2002).

In several tissues, like liver, spleen or placenta, Hybrid-R are more represented than IGF-IR (Bailyes et al., 1997). As tumor tissues overexpress, or present an abnormal activation, both IGF-IR and IR-A (Frasca et al., 1999; Sciacca et al., 1999, Oncogene 18, 2471-2479; Vella et al., 2001, Mol. Pathol., 54, 121-124), Hybrid-RsA may also be overexpressed in a variety of human malignancies, including thyroid and breast cancers providing a selective growth advantage to malignant cells able to respond by a type IGF-IR signalisation following a stimulation by IGF1 and/or IGF2 but also by insulin at physiological concentrations (Bailyes et al., 1997; Pandini et al., 1999, Clin. Cancer Res., 5, 1935-1944; Belfiore et al., 1999, Biochimie (Paris) 81, 403-407; Frasca et al. 1999, Sciacca et al., 1999; Vella et al., 2001).

The realisation of such "therapeutic tools" able to block in the same time the two receptors is of particular interest as they will allow to avoid the escape phenomena mediated by the expression, or abnormal activation, in a same tumor of IGF-IR and hybrid-R.

Regarding the increasing interest on IGF-IR and, more particularly, monoclonal antibodies able to bind to, or inhibit the tyrosine kinase activity of, IGF-IR, the applicants have already developed and characterized a humanized monoclonal antibody called 7C10 or h7C10 (coded F50035). An international patent application PCT/FR 03/00178 relating to this antibody and its uses have been filed and published on 24 Jul. 2003 under the publication number WO 03/059951. The content of this patent application is incorporated herein by reference.

BRIEF SUMMARY OF THE INVENTION

The object of the present invention is to be able to have available other murine monoclonal antibodies, preferably chimerized or humanized antibodies, which will recognize IGF-IR specifically and with great affinity. These antibodies will interact little or not at all with the IR. Their attachment will be able to inhibit in vitro the growth of tumors expressing IGF-IR by interacting principally with the signal transduction pathways activated during IGF1/IGF-IR and IGF2/IGF-IR interactions. These antibodies will be able to be active in vivo on all the types of tumors expressing IGF-IR including estrogen-dependent tumors of the breast and tumors of the prostate.

The present invention also allows to jointly block the hybrid-R and IGF-IR activity by generating a compound, and more particularly antibodies, of high affinity able to bind to said two receptors and also to block their activation by IGF1, IGF2 or Insulin.

The present invention also deals with the use of isolated antibodies according to the present invention, or a fragment thereof, said antibodies or fragment being able to bind to i) human IGF-IR ,and/or to inhibit the binding of its native ligands, preferably IGF1 and/or IGF2, and/or also able to inhibit specifically the tyrosine kinase activity of said IGF-IR and/or ii) hybrid-R, and/or to inhibit the binding of its native ligands, preferably IGF1, IGF2 and/or Insulin, and/or also able to specifically inhibit the tyrosine kinase activity of said hybrid-R.

According to another preferred embodiment, said antibodies are used for cancer therapy, more particularly breast cancer therapy.

Actually, it is known that breast tumoral cells specifically present on their surface IGF-IR but also a great number of Insulin receptor and, as a consequence, a great number of Hybrid-R (Frasca et al., 1999; Sciacca et al., 1999; Vella et al., 2001).

More particularly, the present invention concerns four different anti-IGF-IR monoclonal antibodies.

DETAILED DESCRIPTION OF THE INVENTION

Figure 1:
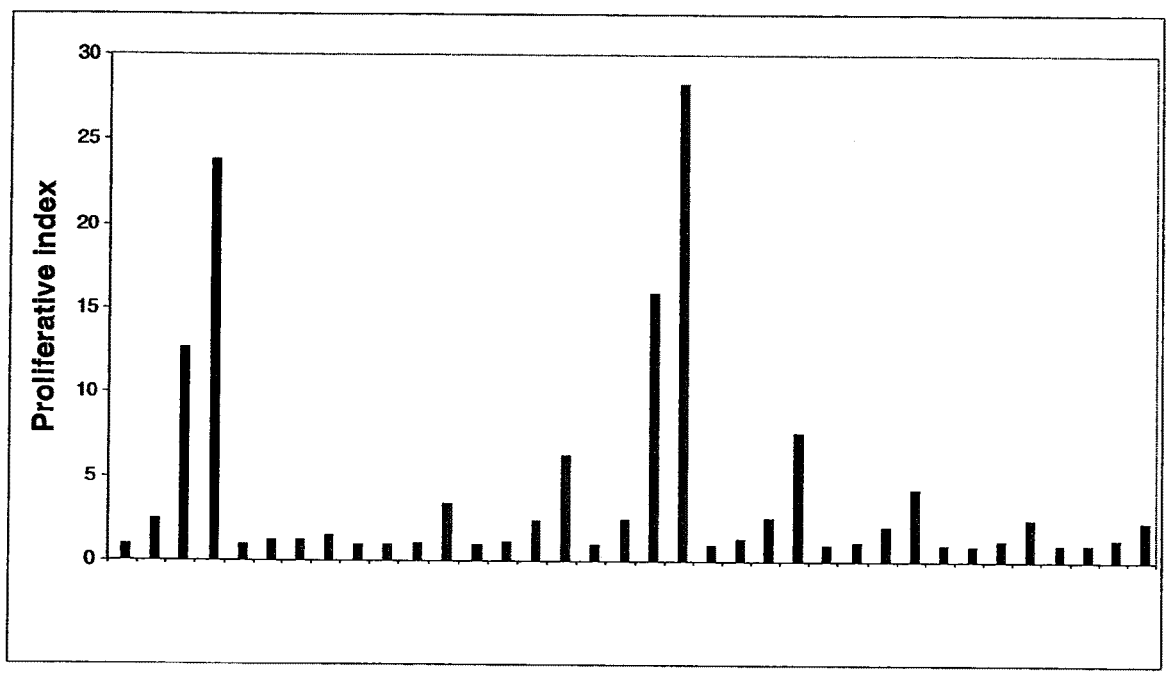
FIG. 1 represents the in vitro evaluation of anti IGF-1R antibodies in the MCF-7 model.

In a first aspect, a subject of the present invention is an isolated antibody, or one of its functional fragments, said antibody or one of its said fragments being capable of binding specifically to the human insulin-like growth factor I receptor and, if necessary, preferably moreover capable of inhibiting the natural attachment of the ligands IGF1 and/or IGF2 of IGF-IR and/or capable of specifically inhibiting the tyrosine kinase activity of said IGF-IR, characterized in that it comprises a light chain comprising at least one complementarity determining region CDR chosen from the CDRs of amino acid sequence SEQ ID Nos. 1, 2 and 3, or at least one CDR whose sequence has at least 80%, preferably 85%, 90%, 95% and 98% identity, after optimum alignment, with the sequence SEQ ID Nos. 1, 2 and 3, or in that it comprises a heavy chain comprising at least one CDR chosen from the CDRs of amino acid sequence SEQ ID Nos. 4, 5 and 6, or at least one CDR whose sequence has at least 80%, preferably 85%, 90%, 95% and 98% identity, after optimum alignment, with the sequence SEQ ID No. 4, 5 and 6.

In the present specification and corresponding exemples, this antibody will be referred as 13F5.

In the present description, the terms "to bind" and "to attach" have the same meaning and are inter-changeable.

In the present description, the terms polypeptides, polypeptide sequences, peptides and proteins attached to antibody compounds or to their sequence are interchangeable.

It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described further on.

By CDR regions or CDR(s), it is intended to indicate the hypervariable regions of the heavy and light chains of the immunoglobulins as defined by Kabat et al. (Kabat et al., Sequences of proteins of immunological interest, 5th Ed., U.S. Department of Health and Haman Services, NIH, 1991, and later editions). Three heavy chain CDRs and 3 light chain CDRs exist. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

By "percentage of identity" between two nucleic acid or amino acid sequences in the sense of the present invention, it is intended to indicate a percentage of nucleotides or of identical amino acid residues between the two sequences to be compared, obtained after the best alignment (optimum alignment), this percentage being purely statistical and the differences between the two sequences being distributed randomly and over their entire length. The comparisons of sequences between two nucleic acid or amino acid sequences are traditionally carried out by comparing these sequences after having aligned them in an optimum manner, said comparison being able to be carried out by segment or by "comparison window". The optimum alignment of the sequences for the comparison can be can carried out, in addition to manually, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444), by means of computer software using these algorithms (GAP, BES PIT, PASTA and TFASTA in the Wisconsin Genetics Software Package, Genetics Computer Group, 575 Science Dr., Madison, Wis., or else by BLAST N or BLAST P comparison software).

The percentage of identity between two nucleic acid or amino acid sequences is determined by comparing these two sequences aligned in an optimum manner and in which the nucleic acid or amino acid sequence to be compared can comprise additions or deletions with respect to the reference sequence for an optimum alignment between these two sequences. The percentage of identity is calculated by determining the number of identical positions for which the nucleotide or the amino acid residue is identical between the two sequences, by dividing this number of identical positions by the total number of positions in the comparison window and by multiplying the result obtained by 100 in order to obtain the percentage of identity between these two sequences.

For example, it is possible to use the BLAST program, "BLAST 2 sequences" (Tatusova et al., "Blast 2 sequences—a new tool for comparing protein and nucleotide sequences", FEMS Microbiol Lett. 174:247-250) available on the site www.ncbi.nlm.nih.gov/gorf/b12.html, the parameters used being those given by default (in, particular for the parameters "open gap penalty": 5, and "extension gap penalty": 2; the matrix chosen being, for example, the matrix "BLOSUM 62" proposed by the program), the percentage of identity between the two sequences to be compared, being calculated directly by the program.

By amino acid sequence having at least 80%, preferably 85%, 90%, 95% and 98% identity with a reference amino acid sequence, those having, with respect to the reference sequence, certain modifications, in particular a deletion, addition or substitution of at least one amino acid, a truncation or an elongation are preferred. In the case of a substitution of one or more consecutive or nonconsecutive amino acid(s), the substitutions are preferred in which the substituted amino acids are replaced by "equivalent" amino acids. The expression "equivalent amino acids" is aimed here at indicating any amino acid capable of being substituted with one of the amino acids of the base structure without, however, essentially modifying the biological activities of the corresponding antibodies and such as will, be defned later, especially in the examples. These equivalent amino acids can be determined either by relying on their these algorithms (GAP, BESTFIT, FASTA and TFASTA in the Wisconsin Genetics Software Package, Genetics Computer Group, 575 Science Dr., Madison, Wis., or else by BLAST N or BLAST P comparison software).

The percentage of identity between two nucleic acid or amino acid sequences is determined by comparing these two sequences aligned in an optimum manner and in which the nucleic acid or amino acid sequence to be compared can comprise additions or deletions with respect to the reference sequence for an optimum alignment between these two sequences. The percentage of identity is calculated by determining the number of identical positions for which the nucleotide or the amino acid residue is identical between the two sequences, by dividing this number of identical positions by the total number of positions in the comparison window and by multiplying the result obtained by 100 in order to obtain the percentage of identity between these two sequences.

For example, it is possible to use the BLAST program, "BLAST 2 sequences" (Tatusova et al., "Blast 2 sequences—a new tool for comparing protein and nucleotide sequences", FEMS Microbiol Lett. 174:247-250) available on the site http://www.ncbi.ncbi.nlm.nih.gov/gorf/b12.html; the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

By amino acid. sequence having at least 80%, preferably 85%, 90%, 95% and 98% identity with a reference amino acid sequence, those having, with respect to the reference sequence, certain modifications, in particular a deletion, addition or substitution of at least one amino acid, a truncation or an elongation are preferred. In the case of a substitution of one or more consecutive or nonconsecutive amino acid(s), the substitutions are preferred in which the substituted amino acids are replaced by "equivalent" amino acids. The expression "equivalent amino acids" is aimed here at indicating any amino acid capable of being substituted with one of the amino acids of the base structure without, however, essentially modifying the biological activities of the corresponding antibodies and such as will be defined later, especially in the examples. These equivalent amino acids can be determined either by relying on their structural homology with the amino acids which they replace, or on results of comparative trials of biological activity between the different antibodies capable of being carried out.

By way of example, mention is made of the possibilities of substitution capable of being carried out without resulting in a profound modification of the biological activity of the corresponding modified antibody. It is thus possible to replace leucine by valine or isoleucine, aspartic acid by glutamic acid, glutamine by asparagine, arginine by lysine, etc., the reverse substitutions being naturally envisageable under the same conditions.

In a second aspect, a subject of the present invention is an isolated antibody, or one of its functional fragments, said antibody or one of its said fragments being capable of binding specifically to the human insulin-like growth factor I receptor and, if necessary, preferably moreover capable of inhibiting the natural attachment of the ligands IGF1 and/or IGF2 of IGF-IR and/or capable of specifically inhibiting the tyrosine kinase activity of said IGF-IR, characterized in that it comprises a light chain comprising at least one complementarity determining region CDR chosen from the CDRs of amino acid sequence SEQ ID Nos. 7, 8 and 9, or at least one CDR whose sequence has at least 80%, preferably 85%, 90%, 95% and 98% identity, after optimum alignment, with the sequence SEQ ID Nos. 7, 8 and 9, or in that it comprises a heavy chain comprising at least one CDR chosen from the CDRs of amino acid sequence SEQ ID Nos. 10, 11 and 12, or at least one CDR whose sequence has at least 80%, preferably 85%, 90%, 95% and 98% identity, after optimum alignment, with the sequence SEQ ID Nos. 10, 11 and 12.

In the following specification, this antibody will be referred as 12D5.

In a third aspect, a subject of the present invention is an isolated antibody, or one of its functional fragments, said antibody or one of its said fragments being capable of binding specifically to the human insulin-like growth factor I receptor and, if necessary, preferably moreover capable of inhibiting the natural attachment of the ligands IGF1 and/or IGF2 of IGF-IR and/or capable of specifically inhibiting the tyrosine kinase activity of said IGF-IR, characterized in that it comprises a light chain comprising at least one complementarity determining region CDR chosen from the CDRs of amino acid sequence SEQ ID Nos. 13, 14 and 15, or at least one CDR whose sequence has at least 80%, preferably 85%, 90%, 95% and 98% identity, after optimum alignment, with the sequence SEQ ID Nos. 13, 14 and 15, or in that it comprises a heavy chain comprising at least one CDR chosen from the CDRs of amino acid sequence SEQ ID Nos. 16, 17 and 18, or at least one CDR whose sequence has at least 80%, preferably 85%, 90%, 95% and 98% identity, after optimum alignment, with the sequence SEQ ID Nos. 16, 17 and 18.

In the following specification, this antibody will be referred as 2D10.

Last, in yet another aspect, a subject of the present invention is an isolated antibody, or one of its functional fragments, capable of binding specifically to the human insulin-like growth factor I receptor and, if necessary, preferably moreover capable of inhibiting the natural attachment of the ligands IGF1 and/or IGF2 of IGF-IR and/or capable of specifically inhibiting the tyrosine kinase activity of said IGF-IR, characterized in that it consists in the antibody called 21E3 and registered at the CNCM as thereafter mentioned.

The antibodies according to the present invention, i.e. 13F5, 12D5,2D10 and 21E3 are preferably specific monoclonal antibodies, especially of murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein (Nature, 256:495-497, 1975).

The monoclonal antibodies according to the invention can be obtained, for example, from an animal cell immunized against the IGF-IR, or one of its fragments containing the epitope specifically recognized by said monoclonal antibodies according to the invention. Said IGF-IR, or one of its said fragments, can especially be produced according to the usual working methods, by genetic recombination starting with a nucleic acid sequence contained in the cDNA sequence coding for the IGF-IR or by peptide synthesis starting from a sequence of amino acids comprised in. the peptide sequence of the IGF-IR.

The monoclonal antibodies according to the invention can, for example, be purified on an affinity column on which the IGF-IR or one of its fragments containing the epitope specifically recognized by said monoclonal antibodies according to the invention has previously been immobilized. More particularly, said monoclonal antibodies can be purified by chromatography on protein A and/or G, followed or not followed by ion-exchange chromatography aimed at eliminating the residual protein contaminants as well as the DNA and the LPS, in itself followed or not followed by exclusion chromatography on Sepharose gel in order to eliminate the potential aggregates due to the presence of dimers or of other multimers. In an even more preferred manner, the whole of these techniques can be used simultaneously or successively.

Chimeric or humanized antibodies are likewise included in antibodies according to the present invention.

By chimeric antibody, it is intended to indicate an antibody which contains a natural variable (light chain and heavy chain) region derived from an antibody of a given species in combination with the light chain and heavy chain constant regions of an antibody of a species heterologous to said given species.

The antibodies or their fragments of chimeric type according to the invention can be prepared by using the techniques of genetic recombination. For example, the chimeric antibody can be produced by cloning a recombinant DNA containing a promoter and a sequence coding for the variable region of a non-human, especially murine, monoclonal antibody according to the invention and a sequence coding for the constant region of human antibody. A chimeric antibody of the invention encoded by such a recombinant gene will be, for example, a mouse-man chimera, the specificity of this antibody being determined by the variable region derived from the murine DNA and its isotype determined by the constant region derived from the human DNA. For the methods of preparation of chimeric antibodies, it is possible, for example, to refer to the document Verhoeyn et al. (BioEssays, 8:74, 1988).

By humanized antibody, it is intended to indicate an antibody which contains CDR regions derived from an antibody of nonhuman. origin, the other parts of the antibody molecule being derived from one (or from several) human antibodies. Moreover, some of the residues of the segments of the skeleton (called FR) can be modified in order to conserve the affinity of the binding (Jones et al., Nature, 321:522-525, 1986; Verhoeyen et al., Science, 239:1534-1536, 1988; Riechmann et al., Nature, 332:323-327, 1988).

The humanized antibodies according to the invention or their fragments can be prepared by techniques known to the person skilled in the art (such as, for example, those described in the documents Singer et al., J. Immun. 150:2844-2857, 1992; Mountain et al., Biotechnol. Genet. Eng. Rev., 10: 1-142, 1992; or Bebbington et al., Bio/Technology, 10:169-175, 1992). Such humanized antibodies according to the invention are preferred for their use in in vitro diagnostic methods, or in vivo prophylactic and/or therapeutic treatment.

By functional fragment of an antibody according to the invention, it is intended to indicate in particular an antibody fragment, such as Fv, scFv (sc for single chain), Fab, F(ab')$_2$, Fab', scFv-Fc fragments or diabodies, or any fragment of which the half-life time would have been increased by chemical modification, such as the addition of poly(alkylene) glycol such as poly(ethylene) glycol ("PEGylation") (pegylated fragments called Fv-PEG, scFv-PEG, Fab-PEG, F(ab')$_2$-PEG or Fab'-PEG) ("PEG" for Poly(Ethylene) Glycol), or by incorporation in a liposome, said fragments having at least one of the characteristic CDRs of sequence SEQ ID Nos. 1 to 6, 7 to 12 or 13 to 18 according to the invention, and, especially, in that it is capable of exerting in a general rammer an even partial activity of the antibody from which it is descended, such as in particular the capacity to recognize and to bind to the IGF-IR, and, if necessary, to inhibit the activity of the IGF-IR.

Preferably, said fractional fragments will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to 1/100, in a more preferred manner to at least 1/10, of that of the antibody from which it is descended, with respect to the IGF-IR. Such a functional fragment will contain at the minimum 5 amino acids, preferably 10, 15, 25, 50 and 100 consecutive amino acids of the sequence of the antibody from which it is descended.

Preferably, these fractional fragments will be fragments of Fv, scFv, Fab, F(ab')$_2$, F(ab'), scFv-Fc type or diabodies, which generally have the same specificity of binding as the antibody from which they are descended. According to the present invention, antibody fragments of the invention can be obtained starting from antibodies such as described above by methods such as digestion by enzymes, such as pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

More particularly, the invention comprises the antibodies, or their functional fragments, according to the present invention, especially chimeric or humanized antibodies, obtained by genetic recombination or by chemical synthesis.

According a first approach, the antibody will be define by its heavy chain sequence.

In a first preferred manner, the present invention relates to an antibody or one of its functional fragments, according to the invention, characterized in that it comprises a heavy chain comprising at least two of the three CDRs or the three CDRs of sequence SEQ ID Nos. 4 to 6, or at least two of three CDRs or three CDRs of sequence respectively having at least 80% identity after optimum alignment with the sequence SEQ ID Nos. 4 to 6.

In a second preferred manner, the present invention relates to an antibody or one of its functional fragments, according to the invention, characterized in that it comprises a heavy chain comprising at least two of the three CDRs or the three CDRs of sequence SEQ ID Nos. 10 to 12, or at least two of three CDRs or three CDRs of sequence respectively having at least 80% identity after optimum alignment with the sequence SEQ ID Nos. 10 to 12.

In a third preferred manner, the present invention relates to an antibody or one of its functional fragments, according to the invention, characterized in that it comprises a heavy chain comprising at least two of the three CDRs or the three CDRs of sequence SEQ ID Nos. 16 to 18, or at least two of three CDRs or three CDRs of sequence respectively having at least 80% identity after optimum alignment with the sequence SEQ ID Nos. 16 to 18.

According a second approach, the antibody will be now define by its light chain sequence.

In a likewise preferred first embodiment, the antibody or one of its functional fragments, according to the invention, is characterized in that it comprises a light chain comprising at least one CDR chosen from the CDRs of sequence SEQ ID Nos. 1 to 3, or a CDR whose sequence has at least 80% identity after optimum alignment with the sequence SEQ ID Nos. 1 to 3.

In a second embodiment, the antibody or one of its functional fragments, according to the invention, is characterized in that it comprises a light chain comprising at least one CDR chosen- from the CDRs of sequence SEQ ID Nos. 7 to 9, or a CDR whose sequence has at least 80% identity after optimum alignment with the sequence SEQ ID Nos. 7 to 9.

In a third preferred embodiment, the antibody or one of its functional fragments, according to the invention, is characterized in that it comprises a light chain comprising at least one CDR chosen from the CDRs of sequence SEQ ID Nos. 13 to 15, or a CDR whose sequence has at least 80% identity after optimum alignment with the sequence SEQ ID Nos. 13 to 15.

According a third approach, the antibody will be now define both by its light chain sequence and its heavy chain sequence.

In a first preferred manner, the antibody or one of its functional fragments according to the invention is characterized in that it comprises a heavy chain comprising the three CDRs of sequence SEQ ID Nos. 4 to 6, or three CDRs of sequence having at least 80% of identity after optimum alignment with the sequence SEQ ID Nos. 4 to 6, and in that it moreover comprises a light chain comprising the three CDRs of sequence SEQ ID Nos. 1 to 3, or three CDRs of sequence having at least 80% of identity after optimum alignment with the sequence SEQ ID Nos. 1 to 3.

In a second preferred manner, the antibody or one of its functional fragments according to the invention is characterized in that it comprises a heavy chain comprising the three CDRs of sequence SEQ ID Nos. 10 to 12, or three CDRs of sequence having at least 80% of identity after optimum alignment with the sequence SEQ ID No. 10 to 12 and in that it moreover comprises a light chain comprising the three CDRs of sequence SEQ ID Nos. 7 to 9, or three CDRs of sequence having at least 80% of identity after optimum alignment with the sequence SEQ ID Nos. 7 to 9.

In a third preferred manner, the antibody or one of its functional fragments according to the invention is characterized in that it comprises a heavy chain comprising the three CDRs of sequence SEQ ID Nos. 16 to 18, or three CDRs of sequence having at least 80% of identity after optimum alignment with the sequence SEQ ID No. 16 to 18 and in that it moreover comprises a light chain comprising the three CDRs of sequence SEQ ID Nos. 13 to 15, or three CDRs of sequence having at least 80% of identity after optimum alignment with the sequence SEQ ID Nos. 13 to 15.

In yet another preferred embodiment, the antibody or one of its functional fragments according to the invention and called 13F5 is characterized in that it comprises a heavy chain of sequence comprising the amino acid sequence SEQ ID No. 20, and in that it moreover comprises a light chain of sequence comprising the amino acid sequence SEQ ID No. 19.

In yet another preferred embodiment, the antibody or one of its functional fragments according to the invention and called 12D5 is characterized in that it comprises a heavy chain of sequence comprising the amino acid sequence SEQ ID No. 22 or 23, and in that it moreover comprises a light chain of sequence comprising the amino acid sequence SEQ ID No. 21.

In yet another preferred embodiment, the antibody or one of its functional fragments according to the invention and called 2D10 is characterized in that it comprises a heavy chain of sequence comprising the amino acid sequence SEQ ID No. 25, and in that it moreover comprises a light chain of sequence comprising the amino acid sequence SEQ ID No. 24.

Another possibility, part of the present invention, is an antibody wherein the three CDRs of the heavy chain are randomly chosen in the group comprising the CDRs of each 13F5, 12D5 and 2D10 and wherein the three CDRs of the lignt chain are also randomly chosen in the group comprising the CDRs of each 13F5, 12D5 and 2D10.

According to another aspect, a subject of the present invention is an antibody or one of its functional fragments, according to the invention, characterized in that it does not attach or it does not attach in a significant manner to the human insulin receptor IR.

In a preferred manner, said functional fragments according to the present invention will be chosen from the fragments Fv, scFv, Fab, (Fab')$_2$, Fab', scFv-Fc or diabodies, or any functional fragment whose half-life would have been increased by a chemical modification, especially by PEGylation, or by incorporation in a liposome.

According to another aspect, the invention relates to murine hybridoma capable of secreting monoclonal antibodies according to the present invention, especially hybridoma of murine origin such as deposited at the Centre National de Cultures de Microorganismes (CNCM, National Center of Microorganism Cultures) (Institut Pasteur, 25 rue du Docteur Roux, F75724 Paris Cedex 15, France).

The monoclonal antibody here called 13F5, or one of its functional fragments, characterized in that said antibody is secreted by the hybridoma deposited at the CNCM on Mar. 25, 2004 under the number CNCM I-3193 is, of course, part of the present invention. This hybridoma consists in a murine hybridoma resulting in the cellular fusion of immunized mouse splenocytes with a myeloma cell line (Sp20 Ag14).

The monoclonal antibody here called 12D5, or one of its functional fragments, characterized in that said antibody is secreted by the hybridoma deposited at the CNCM on Apr. 8, 2004 under the number CNCM I-3195 is, of course, part of the present invention. This hybridoma consists in a murine hybridoma resulting in the cellular fusion of immunized mouse splenocytes with a myeloma cell line (Sp20 Ag14).

The monoclonal antibody here called 2D10, or one of its functional fragments, characterized in that said antibody is secreted by the hybridoma deposited at the CNCM on 13 May 2004 under the number I-3214 is, of course, part of the present invention. This hybridoma also consists in a murine hybridoma resulting in the cellular fusion of immunized mouse splenocytes with a myeloma cell line (Sp20 Ag14).

The monoclonal antibody here called 21E3, or one of its functional fragments, characterized in that said antibody is secreted by the hybridoma deposited at the CNCM on 1 Jul. 2004 under the number I-3249 is, of course, part of the present invention. This hybridoma also consists in a murine hybridoma resulting in the cellular fusion of immunized mouse splenocytes with a myeloma cell line (8p20 Ag14). According to a likewise particular aspect, the present invention relates to a chimeric antibody, or one of its functional fragments, according to the invention, characterized in that said antibody moreover comprises the light chain and heavy chain constant regions derived from an antibody of a species heterologous to the mouse, especially man, and in a preferred manner in that the light chain and heavy chain constant regions derived from a human antibody are respectively the kappa and gamma-1, gamma-2 or gamma-4 region.

According to a novel aspect, the present invention relates to an isolated nucleic acid, characterized in that it is chosen from the following nucleic acids:

a) a nucleic acid, DNA or RNA, coding for an antibody, or one of its functional fragments, according to the invention;

b) a complementary nucleic acid of a nucleic acid such as defined in a).

By nucleic acid, nucleic or nucleic acid sequence, polynucleotide, oligonucleotide, polynucleotide sequence, nucleotide sequence, terms which will be employed indifferently in the present invention, it is intended to indicate a precise linkage of nucleotides, which are modified or unmodified, allowing a fragment or a region of a nucleic acid to be defined, containing or not containing unnatural nucleotides, and being able to correspond just as well to a double-stranded DNA, a single-stranded DNA as to the transcription products of said DNAs.

It must also be understood here that the present invention does not concern the nucleotide sequences in their natural chromosomal environment, that is to say in the natural state. It concerns sequences which have been isolated and/or purified, that is to say that they have been selected directly or indirectly, for example by copy, their environment having been at least partially modified. It is thus likewise intended to indicate here the isolated nucleic acids obtained by genetic recombination by means, for example, of host cells or obtained by chemical synthesis.

A hybridization under conditions of high stringency signifies that the temperature conditions and ionic strength conditions are chosen in such a way that they allow the maintenance of the hybridization between two fragments of complementary DNA. By way of illustration, conditions of high stringency of the hybridization step for the purposes of defining the polynucleotide fragments described above are advantageously the following.

The DNA-DNA or DNA-RNA hybridization is carried out in two steps: (1) prehybridization at 42° C. for 3 hours in phosphate buffer (20 mM, pH 7.5) containing 5×SSC (1×SSC corresponds to a 0.15 M NaCl+0.015 M sodium citrate solution), 50% of formamide, 7% of sodium dodecyl sulfate (SDS), 10× Denhardt's, 5% of dextran sulfate and 1% of salmon sperm DNA; (2) actual hybridization for 20 hours at a temperature dependent on the size of the probe (i.e.: 42° C., for a probe size >100 nucleotides) followed by 2 washes of 20 minutes at 20° C. in 2×SSC+2% of SDS, 1 wash of 20 minutes at 20° C. in 0.1×SSC+0.1% of SDS. The last wash is carried out in 0.1×SSC+0.1% of SDS for 30 minutes at 60° C. for a probe size >100 nucleotides. The hybridization conditions of high stringency described above for a polynucleotide of defined size can be adapted by the person skilled in the art for oligonucleotides of greater or smaller size, according to the teaching of Sambrook et al. (1989, Molecular cloning: a laboratory manual. 2nd Ed. Cold Spring Harbor).

The invention likewise relates to a vector comprising a nucleic acid according to the present invention.

The invention aims especially at cloning and/or expression vectors which contain a nucleotide sequence according to the invention.

The vectors according to the invention preferably contain elements which allow the expression and/or the secretion of the nucleotide sequences in a determined host cell. The vector must therefore contain a promoter, signals of initiation and termination of translation, as well as appropriate regions of regulation of transcription. It must be able to be maintained in a stable manner in the host cell and can optionally have particular signals which specify the secretion of the translated protein. These different elements are chosen and optimized by the person skilled in the art as a function of the host cell used. To this effect, the nucleotide sequences according to the invention can be inserted into autonomous replication vectors in the chosen host, or be integrative vectors of the chosen host.

Such vectors are prepared by methods currently used by the person skilled in the art, and the resulting clones can be introduced into an appropriate host by standard methods, such as lipofection, electroporation, thermal shock, or chemical methods.

The vectors according to the invention are, for example, vectors of plasmidic or viral origin. They are useful for transforming host cells in order to clone or to express the nucleotide sequences according to the invention.

The invention likewise comprises the host cells transformed by or comprising a vector according to the invention.

The host cell can be chosen from prokaryotic or eukaryotic systems, for example bacterial cells but likewise yeast cells or animal cells, in particular mammalian cells. It is likewise possible to use insect cells or plant cells.

The invention likewise concerns animals, except man, which comprise at least one cell transformed according to the invention.

According to another aspect, a subject of the invention is a process for production of an antibody, or one of its functional fragments according to the invention, characterized in that it comprises the following stages:

a) culture in a medium and appropriate culture conditions of a host cell according to the invention; and b) the recovery of said antibodies, or one of their functional fragments, thus produced starting from the culture medium or said cultured cells.

The cells transformed according to the invention can be used in processes for preparation of recombinant polypeptides according to the invention. The processes for preparation of a polypeptide according to the invention in recombinant form, characterized in that they employ a vector and/or a cell transformed by a vector according to the invention, are themselves comprised in the present invention. Preferably, a cell transformed by a vector according to the invention is cultured under conditions which allow the expression of said polypeptide and said recombinant peptide is recovered.

As has been said, the host cell can be chosen from prokaryotic or eukaryotic systems. In particular, it is possible to identify nucleotide sequences according to the invention, facilitating secretion in such a prokaryotic or eukaryotic system. A vector according to the invention carrying such a sequence can therefore advantageously be used for the production of recombinant proteins, intended to be secreted. In effect, the purification of these recombinant proteins of interest will be facilitated by the fact that they are present in the supernatant of the cell culture rather than in the interior of the host cells.

It is likewise possible to prepare the polypeptides according to the invention by chemical synthesis. Such a preparation process is likewise a subject of the invention. The person skilled in the art knows the processes of chemical synthesis, for example the techniques employing solid phases (see especially Steward et al., 1984, Solid phase peptide synthesis, Pierce Chem. Company, Rockford, 111, 2nd ed.) or techniques using partial solid phases, by condensation of fragments or by a classical synthesis in solution. The polypeptides obtained by chemical synthesis and being able to contain corresponding unnatural amino acids are likewise comprised in the invention.

The antibodies, or one of their functional fragments, capable of being obtained by a process according to the invention are likewise comprised in the present invention.

According to a second embodiment, the present invention concerns an antibody according to the invention such as described further above, characterized in that it is, moreover, capable of binding specifically to the human epidermal growth factor receptor EGFR and/or capable of specifically inhibiting the tyrosine kinase activity of said EGFR.

The invention likewise concerns a pharmaceutical composition comprising by way of active principle a compound consisting of an antibody, or one of its functional fragments according to the invention, preferably mixed with an excipient and/or a pharmaceutically acceptable vehicle.

Another complementary embodiment of the invention consists in a composition such as described above which comprises, moreover, as a combination product for simultaneous, separate or sequential use, a cytotoxic/cytostatic agent and/or an inhibitor of the tyrosine kinase activity respectively of the receptors for IGF-I and/or for EGF.

"Simultaneous use" is understood as meaning the administration of the two compounds of the composition according to the invention in a single and identical pharmaceutical form.

"Separate use" is understood as meaning the administration, at the same time, of the two compounds of the composition according to the invention in distinct pharmaceutical forms.

"Sequential use" is understood as meaning the successive administration of the two compounds of the composition according to the invention, each in a distinct pharmaceutical form.

In a general fashion, the composition according to the invention considerably increases the efficacy of the treatment of cancer. In other words, the therapeutic effect of the anti-IGF-IR antibodies according to the invention is potentiated in an unexpected manner by the administration of a cytotoxic agent. Another major subsequent advantage produced by a composition according to the invention concerns the possibility of using lower efficacious doses of active principle, which allows the risks of appearance of secondary effects to be avoided or to be reduced, in particular the effects of the cytotoxic agent.

In addition, this composition according to the invention would allow the expected therapeutic effect to be attained more rapidly.

In a particularly preferred embodiment, said composition as a combination product according to the invention is characterized in that said cytotoxic/cytostatic agent is chosen from the agents interacting with DNA, the antimetabolites, the topoisomerase I or II inhibitors, or else the spindle inhibitor or stabilizer agents or else any agent capable of being used in chemotherapy. Such cytotoxic/cytostatic agents, for each of the aforesaid classes of cytotoxic agents, are, for example, cited in the 2001 edition of VIDAL, on the page devoted to the compounds attached to the cancerology and hematology column "Cytotoxice", these cytotoxic compounds cited with reference to this document are cited here as preferred cytotoxic agents.

In a particularly preferred embodiment, said composition as a combination product according to the invention is characterized in that said cytotoxic agent is coupled chemically to said antibody for simultaneous use.

In a particularly preferred embodiment, said composition according to the invention is characterized in that said cytotoxic/cytostatic agent is chosen from the spindle inhibitor or stabilizer agents, preferably vinorelbine and/or vinflunine and/or vincristine.

In order to facilitate the coupling between said cytotoxic agent and said antibody according to the invention, it is especially possible to introduce spacer molecules between the two compounds to be coupled, such as poly(alkylene) glycols like polyethylene glycol, or else amino acids, or, in another embodiment, to use active derivatives of said cytotoxic agents into which would have been introduced functions capable of reacting with said antibody according to the invention. These coupling techniques are well known to the person skilled in the art and will not be expanded upon in the present description.

In another preferred embodiment, said inhibitor of the tyrosine kinase activity of the receptors for IGF-I is selected from the group consisting of derived natural agents, dianilinophthalimides, pyrazolo—or pyrrolopyridopyrimidines or else quinazilines. Such inhibitory agents are well known to the person skilled in the art and described in the literature (Ciardiello F., Drugs 2000, Suppl. 1, 25-32).

According to yet another embodiment of the invention, the composition such as described above can likewise comprise another antibody compound directed against the extracellular domain of the HER2/neu receptor, as a combination product for simultaneous, separate or sequential use, intended for the prevention and for the treatment of cancer, especially the cancers overexpressing said HER2/neu receptor and the receptor IGF-IR, such as especially cancer of the breast.

Reference can be made especially to the publications of Albanell et al. (J. of the National Cancer Institute, 93(24): 1830-1831, 2001) and of Lu et al. (J. of the National Cancer Institute, 93(24):1852-1857, 2001) justifying the unexpected interest in combining an anti-HER2/neu antibody with an anti-IGF-IR antibody according to the present invention.

In a particular manner, said anti-HER2/neu antibody of the composition according to the invention is the antibody called Trastuzumab (also called Herceptin).

The invention relates, in another aspect, to a composition characterized in that one, at least, of said antibodies, or one of their functional fragments, is conjugated with a cell toxin and/or a radioelement Preferably, said toxin or said radioelement is capable of inhibiting at least one cell activity of cells expressing the IGF-IR, in a more preferred manner capable of preventing the growth or the proliferation of said cell, especially of totally inactivating said cell.

Preferably also, said toxin is an enterobacterial toxin, especially Pseudomonas exotoxin A.

The radioelements (or radioisotopes) preferably conjugated to the antibodies employed for the therapy are radioisotopes which emit gamma rays and preferably iodine$^{131}$, yttrium$^{90}$, gold$^{199}$, palladium$^{100}$, copper$^{67}$, bismuth$^{217}$ and antimony$^{211}$. The radioisotopes which emit beta and alpha rays can likewise be used for the therapy.

By toxin or radioelement conjugated to at least one antibody, or one of its functional fragments, according to the invention, it is intended to indicate any means allowing said toxin or said radioelement to bind to said at least one antibody, especially by covalent coupling between the two compounds, with or without introduction of a linking molecule.

Among the agents allowing binding in a chemical (covalent), electrostatic or noncovalent manner of all or part of the components of the conjugate, mention may particularly be made of benzoquinone, carbodiimide and more particularly EDC (1-ethyl-3-[3-dimethylaminopropyl]-carbodiimide hydrochloride), dimalehnide, dithiobis-nitrobenzoic acid (DTNB), N-succinimidyl S-acetyl thio-acetate (SATA), the bridging agents having one or more phenylazide groups reacting with the ultraviolets (U.V.) and preferably N-[-4-(azidosalicylamino)butyl]-3'-(2'-pyridyldithio)-propionamide (APDP), N-succinimid-yl 3-(2-pyridyldithio)propionate (SPDP), 6-hydrazino-nicotinamide (HYNIC).

Another form of coupling, especially for the radioelements, can consist in the use of a bifunctional ion chelator.

Among these chelates, it is possible to mention the chelates derived from EDTA (ethylenediaminetetraacefic acid) or from DTPA (diethylenetriaminepentaacetic acid) which have been developed for binding metals, especially radioactive metals, and immunoglobulins. Thus, DTPA and its derivatives can be substituted by different groups on the carbon chain in order to increase the stability and the rigidity of the ligand-metal complex (Krejcarek et al., 1977; Brechbiel et al., 1991; Gansow, 1991; US Pat. No. 4,831,175).

For example diethylenetriaminepentaacetic acid (DTPA) and its derivatives, which have been widely used in medicine and in biology for a long time either in their free form, or in the form of a complex with a metallic ion, have the remarkable characteristic of forming stable chelates with metallic ions and of being coupled with proteins of therapeutic or diagnostic interest such as antibodies for the development of radioimmoconjugates in cancer therapy (Meases et al., 1984; Gansow et al., 1990).

Likewise preferably, said at least one antibody forming said conjugate according to the invention is chosen from its functional fragments, especially the fragments amputated of their Fc component such as the scFv fragments.

The present invention moreover comprises the use of the composition according to the invention for the preparation of a medicament.

More particularly, according to another embodiment, the invention concerns the use of an antibody, or one of its functional fragments, and/or of a composition for the preparation of a medicament intended for the prevention or for the treatment of an illness induced by an overexpression and/or an abnormal activation of the IGF-I receptor, and/or connected with a hyperactivation of the transduction pathway of the signal mediated by the interaction of the 1-IGF1 or IGF2 with IGF-IR.

Preferably, said use according to the invention is characterized in that the administration of said medicament does not induce or induces only slightly secondary effects connected with inhibition of the insulin receptor IR, that is to say inhibition of the interaction of the IR with its natural ligands due to the presence of said medicament, especially by a competitive inhibition connected with the attachment of said medicament to the IR.

The present invention moreover comprises the use of an antibody, or one of its functional fragments, preferably humanized, and/or of a composition according to the invention for the preparation of a medicament intended to inhibit the transformation of normal cells into cells with tumoral character, preferably IGF-dependent, especially IGF1- and/or IGF2-dependent.

The present invention likewise relates to the use of an antibody, or one of its functional fragments, preferably humanized, and/or of a composition according to the invention for the preparation of a medicament intended to inhibit the growth and/or the proliferation of tumor cells, preferably IGF-dependent, especially IGF1- and/or IGF2-dependent.

In a general manner, a subject of the present invention is the use of an antibody, or one of its functional fragments, preferably humanized, and/or of a composition according to the invention, for the preparation of a medicament intended for the prevention or for the treatment of cancer preferably expressing IGF-IR and/or of cancer preferably having a hyperactivation of the transduction pathway of the signal mediated by the interaction of IGF1 or IGF2 with IGF-IR, such as, for example, the overexpression of IRS1.

The subject of the present invention is likewise the use of an antibody, or one of its functional fragments, preferably humanized, and/or of a composition according to the invention, for the preparation of a medicament intended for the prevention or for the treatment of psoriasis, psoriasis whose epidermal hyperproliferation can be connected with the expression or the overexpression of IGF-IR, and/or with the-hyperactivation of the transduction pathway of the signal mediated by the interaction of IGF-IR with its natural ligands (Wraight C. J. et al., Nat. Biotechnol., 2000, 18(5):521-526. Reversal of epidermal hyperproliferation in psoriasis by insulin-like growth factor I receptor antisense oligonucleotides).

In another embodiment, an object of the invention is the use of an antibody, or one of its functional fragments, preferably humanized, and/or of a composition according to the invention, for the preparation of a medicament intended for the prevention or for the treatment of atherosclerosis.

Among the cancers which can be prevented and/or treated, prostate cancer, osteosarcomas, lung cancer, breast cancer, endometrial cancer or colon cancer or any other cancer overexpressing IGF-IR is preferred.

According to yet another aspect, a subject of the present invention is a method of diagnosis, preferably in vitro, of illnesses connected with an overexpression or an underexpression, preferably an overexpression, of the IGF-I receptor starting from a biological sample in which the abnormal presence of IGF-I receptor is suspected, characterized in that said biological sample is contacted with an antibody, or one of its functional fragments, according to the invention, it being possible for said antibody to be, if necessary, labeled.

Preferably, said illnesses connected with the overexpression of the IGF-I receptor in said diagnosis method will be cancers.

In another particular embodiment, antibodies according to the invention can also be used for the treatment, prevention and/or diagnostic of illness connected with non only the overexpression of the IGF-IR but also the overexpression of Hybrid-R.

More particularly, antibody according to the invention is characterized in that it is also capable of binding to the hybrid-R, isoform(s) A and/or B, and inhibiting the binding of its native ligands, preferably designated herein as IGF1 and/or IGF2 and/or insulin, and/or capable of specifically inhibiting the tyrosine kinase activity of said hybrid-R.

Said antibody, or one of its functional fragments, can be present in the form of an immunoconjugate or of a labeled antibody so as to obtain a detectable and/or quantifiable signal.

The antibodies labeled according to the invention or their functional fragments include, for example, antibodies called immunoconjugates which can be conjugated, for example, with enzymes such as peroxidase, alkaline phosphatase, α-D-galactosidase, glucose oxydase, glucose amylase, carbonic anhydrase, acetylcholinesterase, lysozyme, malate dehydrogenase or glucose 6-phosphate dehydrogenase or by a molecule such as biotin, digoxygenin or 5-bromodeoxyuridine. Fluorescent labels can be likewise conjugated to the antibodies or to their functional fragments according to the invention and especially include fluorescein and its derivatives, fluorochrome, rhodamine and its derivatives, GFP (GFP for "Green Fluorescent Protein"), dansyl, unabelliferone etc. In such conjugates, the antibodies of the invention or their functional fragments can be prepared by methods known to the person skilled in the art. They can be coupled to the enzymes or to the fluorescent labels directly or by the intermediary of a spacer group or of a linking group such as a polyaldehyde, like glutaraldehyde, ethylenediaminetetraacetic acid (EDTA), diethylene-triaminepentaacetic acid (DPTA), or in the presence of coupling agents such as those mentioned above for the therapeutic conjugates. The conjugates containing labels of fluorescein type can be prepared by reaction with an isothiocyanate.

Other conjugates can likewise include chemoluminescent labels such as luminol and the dioxetanes, bio-luminescent labels such as luciferase and luciferin, or else radioactive labels such as iodine$^{123}$, iodine$^{125}$, iodine$^{126}$, iodine$^{133}$, bromine$^{77}$, technetium$^{99m}$, indium$^{111}$, indium$^{113m}$, gallium$^{67}$, gallium$^{68}$, ruthenium$^{95}$, ruthenium$^{97}$, ruthenium$^{103}$, ruthenium$^{105}$, mercury$^{107}$, mercury$^{203}$, rhenium$^{99m}$, rhenium$^{101}$, rhenium$^{105}$, scandium$^{47}$, tellurium$^{121m}$, tellurium$^{122m}$, tellurium$^{125m}$, thulium$^{165}$, thulium$^{167}$, thalium$^{168}$, fluorine$^{18}$, yttrium$^{199}$, iodine$^{131}$. The methods known to the person skilled in the art existing for coupling the therapeutic radio-isotopes to the antibodies either directly or via a chelating agent such as EDTA, DTPA mentioned above can be used for the radioelements which can be used in diagnosis. It is likewise possible to mention labeling with Na[I$^{125}$] by the chloramine T method [Hunter W. M. and Greenwood F. C., 1962, Nature 194:495] or else with technetium$^{99m}$ by the technique of Crockford et al. (U.S. Pat. No. 4,424,200) or attached via DTPA as described by Hnatowich (U.S. Pat. No. 4,479,930).

Thus, the antibodies, or their functional fragments, according to the invention can be employed in a process for the detection and/or the quantification of an overexpression or of an underexpression, preferably an overexpression, of the IGF-I receptor in a biological sample, characterized in that it comprises the following steps:

a) the contacting of the biological sample with an antibody, or one of its functional fragments, according to the invention; and b) the demonstration of the IGF-IR/antibody complex possibly formed.

In a particular embodiment, the antibodies, or their functional fragments, according to the invention, can be employed in a process for the detection and/or the quantification of the IGF-I receptor in a biological sample, for the monitoring of the efficacy of a prophylactic and/or therapeutic treatment of IGF-dependent cancer or else of psoriasis or atherosclerosis.

More generally, the antibodies, or their functional fragments, according to the invention can be advantageously employed in any situation where the expression of the IGF-I receptor must be observed in a qualitative and/or quantitative manner.

Preferably, the biological sample is formed by a biological fluid, such as serum, whole blood, cells, a tissue sample or biopsies of human origin.

Any procedure or conventional test can be employed in order to carry out such a detection and/or dosage. Said test can be a competition or sandwich test, or any test known to the person skilled in the art dependent on the formation of an immune complex of antibody-antigen type. Following the applications according to the invention, the antibody or one of its functional fragments can be immobilized or labeled. This immobilization can be earned out on numerous supports known to the person skilled in the art. These supports can especially include glass, polystyrene, poly-propylene, polyethylene, dextran, nylon, or natural or modified cells. These supports can be either soluble or insoluble.

By way of example, a preferred method brings into play immunoenzymatic processes according to the ELISA technique, by immunofluorescence, or radio-immunoassay (RIA) technique or equivalent.

Thus, the present invention likewise comprises the kits or sets necessary for carrying out a method of diagnosis of illnesses induced by an overexpression or an underexpression of the IGF-I receptor or for carrying out a process for the detection and/or the quantification of an overexpression or of an underexpression of the IGF-I receptor in a biological sample, preferably an overexpression of said receptor, characterized in that said kit or set comprises the following elements:

a) an antibody, or one of its functional fragments, according to the invention;

b) optionally, the reagents for the formation of the medium favorable to the immunological reaction;

c) optionally, the reagents allowing the demonstration of IGF-IR/antibody complexes produced by the immunological reaction.

The invention moreover relates to the use of a composition as a combination product according to the invention, for the preparation of a medicament intended for the prevention or for the treatment of cancer, especially cancers for which said cytotoxic agent or said anti-HER2/neu antibody is generally prescribed and, especially, for which cancers the tumor cells express or overexpress the IGF-I receptor.

A subject of the invention is likewise the use of an antibody according to the invention for the preparation of a medicament intended for the specific targeting of a biologically active compound to cells expressing or overexpressing the IGF-I receptor.

It is intended here by biologically active compound to indicate any compound capable of modulating, especially of inhibiting, cell activity, in particular their growth, their proliferation, transcription or gene translation.

A subject of the invention is also an. in vivo diagnostic reagent comprising an antibody according to the invention, or one of its functional fragments, preferably labeled, especially radiolabeled, and its use in medical imaging, in particular for the detection of cancer connected with the expression or the overexpression by a cell of the IGF-I receptor.

The invention likewise relates to a composition as a combination product or to an anti-IGF-IR/toxin conjugate or radioelement, according to the invention, as a medicament.

Preferably, said composition as a combination product or said conjugate according to the invention will be mixed with an excipient and/or a pharmaceutically acceptable vehicle.

In the present description, pharmaceutically acceptable vehicle is intended to indicate a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles are well known and will be adapted by the person skilled in the art as a function of the nature and of the mode of administration of the active compound(s) chosen.

Preferably, these compounds will be administered by the systemic route, in particular by the intravenous route, by the intramuscular, intradermal, intraperitoneal or subcutaneous route, or by the oral route. In a more preferred manner, the composition comprising the antibodies according to the invention will be administered several times, in a sequential manner.

Their modes of administration, dosages and optimum pharmaceutical forms can be determined according to the criteria generally taken into account in the establishment of a treatment adapted to a patient such as, for example, the age or the body weight of the patient, the seriousness of his/her general condition, the tolerance to the treatment and the secondary effects noted.

Other characteristics and advantages of the invention appear in the continuation of the description with the examples and the figures.

EXAMPLE 1

Generation Of Monoclonal Antibodies Against IGF-1R

Hybridomas were generated by fusion of splenocytes from BALB/c mice immunized with a soluble α2-β2 heterotetrameric recombinant human IGF-1R (R&D System, Minneapolis, USA) and the SP2/0-Ag14 myeloma cell line. The resulting murine antibodies were first screened by ELISA and FACS analysis on MCF-7 cells. Then, a final screen on Sf9-IGF-1r versus Sf9-IR cells was performed to eliminate antibodies recognizing both IGF-1 and IR. The selected MAbs (positives in ELISA and recognizing the wild type receptor on MCF-7 cells) were produced as ascitic fluids and purified by protein A chromatography before testing either in vitro and/or in vivo as summarized in table 1.

TABLE 1

| | Selection of anti-IGF-1R monoclonal antibodies | | | | | |
|---|---|---|---|---|---|---|
| | FACSCAN analysis | | | | In vitro activity | In vivo activity |
| | MCF-7 | Sf9 IGF-1R+ | Sf9 IR+ | Isotype | MCF-7 | DU145 |
| 2D10 | + | + | − | IgG1 κ | + | + |
| 2F2 | + | − | − | IgG1 κ | +/− | +/− |
| 6E5 | + | + | − | IgG1 κ | +/− | + |
| 7A4 | + | + | − | IgG1 κ | − | − |
| 7G3 | + | − | − | IgG1 λ | − | − |
| 9E5 | + | + | − | IgG1 κ | +/− | − |
| 9F5 | + | + | + | Nd | Nd | Nd |
| 10B7 | + | − | − | Nd | Nd | Nd |
| 11H6 | + | + | − | IgE | Nd | − |
| 12B1 | + | + | − | IgG1 κ | + | − |
| 12D5 | + | + | − | IgG1 κ | + | Nd |
| 12D8 | + | Nd | | Nd | Nd | Nd |
| 13F5 | + | + | Nd | IgG1 κ | + | + |
| 13G10 | + | +/− | − | IgG1 λ | +/− | Nd |
| 15B9 | + | + | − | IgG1 κ | +/− | − |
| 16A12 | + | − | + | IgG1 κ | +/− | − |
| 9D5 | + | Nd | − | IgG1 κ | Nd | Nd |
| 14H1 | − | Nd | + | IgG1 κ | Nd | Nd |
| 15H1 | − | Nd | Nd | IgG1 κ | Nd | Nd |
| 18B5 | Nd | Nd | Nd | Nd | Nd | Nd |
| 20D1 | Nd | Nd | Nd | IgG1 κ | Nd | − |
| 21B3 | − | − | − | Nd | Nd | Nd |
| 13F10 | Nd | Nd | Nd | Nd | Nd | Nd |
| 14A1 | − | Nd | Nd | Nd | Nd | Nd |
| 2B10 | + | − | − | IgG1 κ | − | − |
| 3A9 | + | +/− | − | IgG1 κ | Nd | Nd |
| 3C9 | + | + | − | IgG1 κ | − | − |
| 4G4 | + | + | − | IgG1 κ | + | Nd |
| 6F4 | + | − | − | IgG1 κ | +/− | − |
| 9E10 | + | +/− | − | IgG1 λ | +/− | Nd |
| 14D7 | + | + | − | IgG1 κ | Nd | Nd |
| 21E3 | + | − | − | IgG2a | +/− | nd |

EXAMPLE 2

In Vitro Activity Of Anti-IGF-1R Antibodies

Method

MCF-7 cells from ATCC were routinely cultured in phenol red free-RPMI medium (Invitrogen Corporation, Scotland, UK), 10% FCS (Invitrogen Corporation), 1% L-Glutamine (Invitrogen Corporation). MCF-7 cells were plated in 96-well tissue culture plates at a density of $5 \times 10^4$ cells/well in serum-free medium. After 24 hours a dose range of IGF1 from 1 to 50 ng/ml was added to the medium either in absence or in presence at a final concentration of 5 μg/ml of each antibody to be tested. After 3 days, cells were pulsed with 0.5 μCi of [$^3$H]thymidine (Amersham Biosciences AB, Uppsala, Sweden) for 16 hours. The magnitude of [$^3$H]thymidine incorporated into trichloroacetic acid-insoluble DNA was quantified by liquid scintillation counting. Results are expressed as a proliferative index (cpm of cells plus IGF1 plus antibody/cpm of cells plus antibody alone).

Results

The in vitro evaluation was the first screening of Mabs in terms of mitogenic activity. For these assays, the generated antibodies, produced as ascitic fluids, were added to MCF-7 cells at the same time as IGF1 and compared to the commercially available αIR3 Mab to select antibodies at least as efficacious as this latter antibody. The positive Mabs (5 Mabs) described as (+) in Table 2* of the previous reply are the one giving proliferative indexes <5 when cells were stimulated with the highest dose of IGF1 (50 ng/ml). FIG. 1 shows the in vitro activity of four out of the 6 strong in vitro inhibitors (2D10, 12D5, 12B1, 13F5). 2F2 and 21E3 Mabs have been considered as a (±)*Mab (5<Proliferative index<15 for the highest concentration of IGF1) and 7G3 and 2B10 were considered as non-neutralizing antibodies (proliferative index>15). It is interesting to notice that the 21E3 is the only Mab of IgG2 isotype.

EXAMPLE 3

In Vivo Activity Of Anti-IGF-1R Antibodies

Method

DU145 cells from ATCC were routinely cultured in DMEM medium (Invitrogen Corporation, Scotland, UK), 10% FCS (Invitrogen Corporation), 1% L-Glutamine (Invitrogen Corporation). Cells were split two days before engraftment so that they were in exponential phase of growth. Two million DU145 cells were engrafted in PBS to Swiss nude mice. One day after implantation, animals were divided into groups of 6 mice. Mice were treated s.c. at the opposite of the tumor with 200 μg of each antibody to be tested, 3-times a week. The control group was either treated with a murine isotype control (EC2) in the first screening or PBS for subsequent screenings as it has been shown in the first experiment that no difference in tumor growth was observed between these 2 groups of mice. Timor volume was measured once a week and calculated by the formula: $\pi/6 \times length \times width \times height$.

Results

Figure 2:
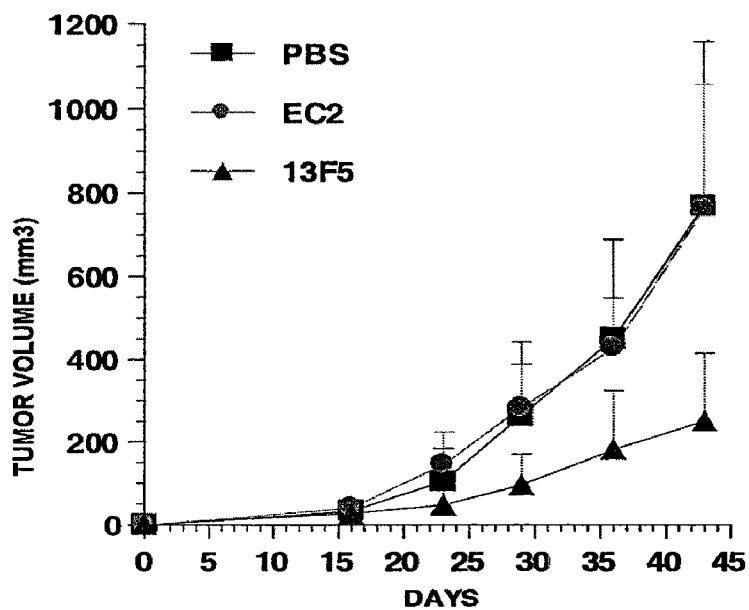
FIGS. 2 and 3 represent in vivo evaluation of anti IGF-1R antibodies on DU145.
Figure 3:
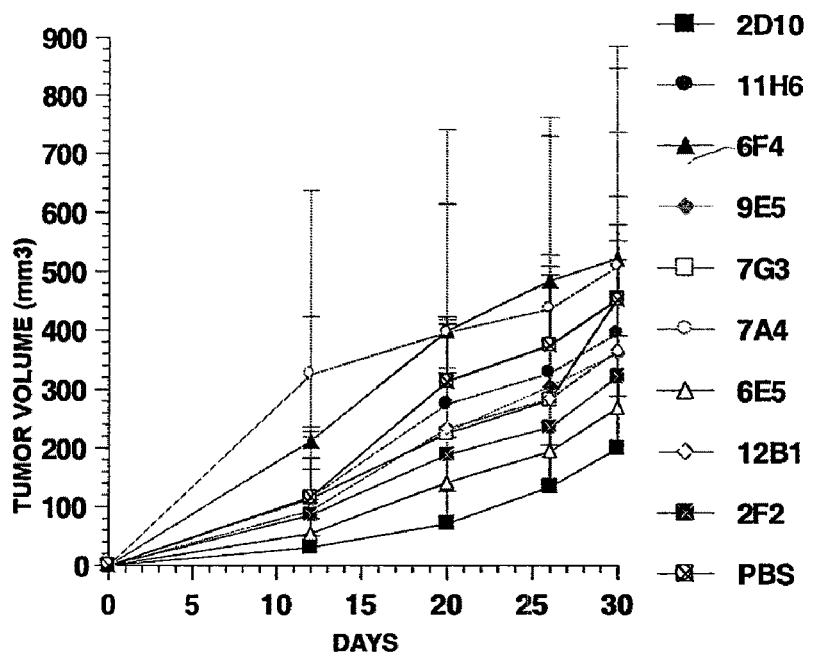

Three in vivo experiments were performed to test a panel of Mabs. FIGS. 2 and 3 show that 13F5, 2D10 and 6E5 significantly inhibit the in vivo growth of DU 145 cells. Statistical analysis (Mann and Whitney test) are shown in Table 2.

TABLE 2

Statistical analysis of in vivo data

|  |  | First screening | D16 | D23 | D29 | D36 | D43 |
|---|---|---|---|---|---|---|---|
| PBS/13F5 | Mann-Whitney (Wilcoxon) | | p = 0.47 | p = 0.086 | p = 0.046 | p = 0.015 | p = 0.023 |
|  |  | Second screening | D12 | D20 | D26 | D30 | |
| PBS/2D10 | Mann-Whitney (Wilcoxon) | | p = 0.0041 | p = 0.0017 | p = 0.0027 | p = 0.0027 | |
| PBS/6E5 | Mann-Whitney (Wilcoxon) | | p = 0.027 | p = 0.013 | p = 0.0092 | p = 0.019 | |
| PBS/12B1 | Mann-Whitney (Wilcoxon) | | p = 0.11 | p = 0.11 | p = 0.067 | p = 0.11 | |
| PBS/2F2 | Mann-Whitney (Wilcoxon) | | p = 0.18 | p = 0.067 | p = 0.050 | p = 0.14 | |
|  |  | Third screening | D12 | D20 | D26 | D33 | |
| PBS/16A12 | Mann-Whitney (Wilcoxon) | | p = 0.063 | p = 0.087 | p = 0.19 | p = 0.11 | |

EXAMPLE 4

Evaluation of 2D10, 12D5, 13F5 Ability to Bind to IGF-IR and Hybrid-R

The used cells far this study are listed thereafter:
R+: R− fibroblasts stably transfected with the IGF-I receptor (IGF-IR) cDNA
R−/1R-A: R− fibroblasts stably transfected with the insulin receptor isoform A (IR-A) cDNA
R−/IR-B: R− fibroblasts stably transfected with the insulin receptor isoform B (IR-B) cDNA
R+/IR-A: R− fibroblasts stably co-transfected with the IGF-I and the iusnlin receptor isoform A cDNA and, therefore, expressing hybrid receptors A (Hybrid-RsA)
R+/IR-B: R− fibroblasts stably co-transfected with the IGF-I and the insulin receptor isoform B cDNA and, therefore, expressing hybrid receptors A (Hybrid-RsB).

EXAMPLE 4-1

Displacement Analysis of [$^{125}$I]IGF1 on IGF-IR by 2D10, 12D5, 13F5 and αIR-3

Figure 4:
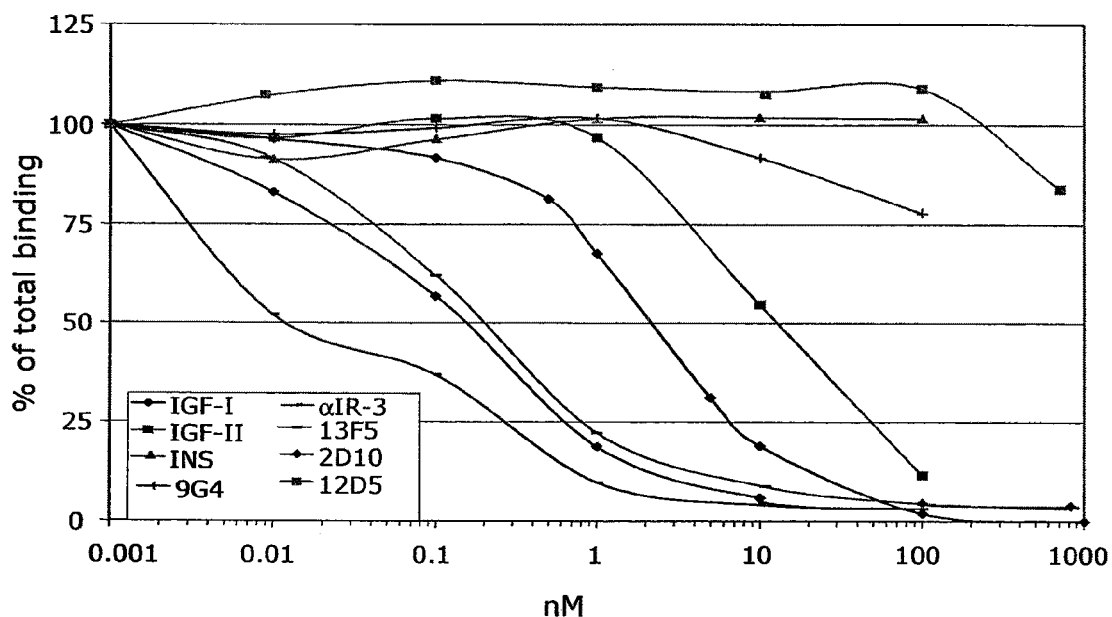
FIG. 4 represents displacement of [$^{125}$I]-IGF-1 on intact cells expressing IGF-IR.

[$^{125}$I]IGF-1 (20,000 cpm) was allowed to bind to R+ intact cells for 16 hours at 4° C., in the absence or presence of increasing concentrations of unlabeled ligand (IGF1, IGF2 or insulin) or antibodies (2D10, 12D5, 13F5). Results are plotted as percent of maximal specific binding and are represented on FIG. 4.

Both 2D10 and 13F5 efficaciously and fully displaced IGF1 with sub-nanomolar affinities and in this example with an $IC_{50}$ of 0.15 and 0.20 nM, respectively, as compared to the reference antibody αIR3 ($IC_{50}$: 0.05 nM). The affinities are higher than those of the natural IGF-IR ligands IGF1 (2.2 nM in this example) and IGF2 (15 nM in this example).

EXAMPLE 4-2

Displacement Analysis of [$^{125}$I]IGF1 on Hybrid-RsA by 2D10, 12D5, 13F5 and 47-9

Hybrid-RsA from R+/IR-A cell lysates were immunocaptured in Maxisorb plates coated with anti IR antibody 83-7.

Figure 5:
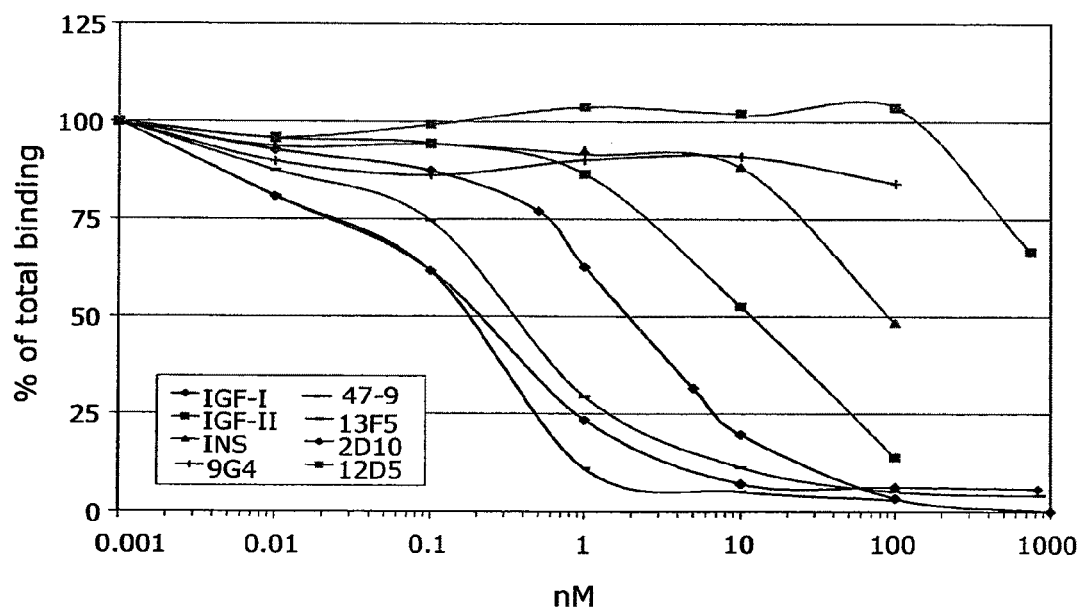
FIG. 5 represents displacement of [$^{125}$I]-IGF-1 on immunocaptured HR-A.

[$^{125}$I]-IGF1 (FIG. 5) was then allowed to bind to immunocaptured receptors in the absence or the presence of increasing concentrations of unlabeled ligand (IGF1, IGF2 or insulin) or antibodies (2D10, 12D5, 13F5, 47-9, 9G4). Results are plotted as percent of maximal specific binding and are represented in FIG. 5.

2D10 and 13F5 displaced efficaciously and fully labeled IGF1 with very similar subnanomolar affinities, and in this example of 0.2 and 0.35 nM respectively. By comparaison, 47-9 yielded an IC$_{50}$ value of 0.18 nM (FIG. 5).

These affinities are higher than those of the natural Hybrid-RsA ligands IGF1 (2.0 nM in this example) and IGF2 (12 nM in this example).

EXAMPLE 4-3

Displacement Analysis of [$^{125}$I]GF1 on Hybrid-RsB by 2D10, 12D5, 13F5 and 47-9

Hybrid RBBB from R+/IR-B cell lysates were immunocaptured in Maxisorb plates coated with 83-7 antibody.

[$^{125}$I]-IGF1 (FIG. 6) was then allowed to bind to immunocaptured receptors in the absence or the presence of increasing concentrations of IGF1, IGF2, insulin or antibodies (2D10, 12D5, 13F5, 47-9, 9G4). Results are plotted as percent of maximal binding.

Figure 6:
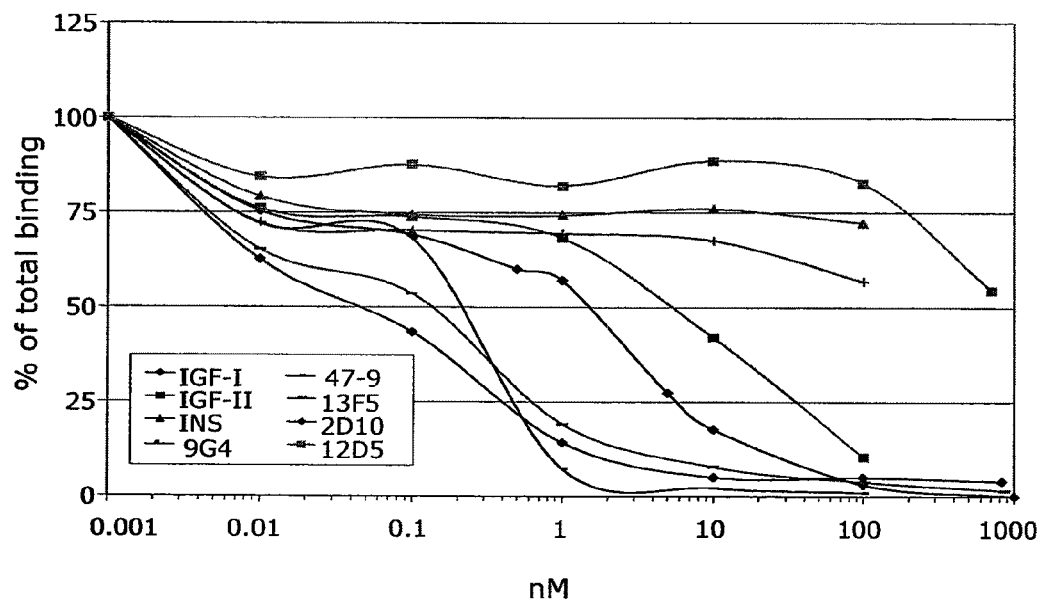
FIG. 6 represents displacement of [$^{125}$I]-IGF-1 on immunocaptured HR-B.

2D10 and 13F5 displaced efficaciously and fully labeled IGF1 with very similar subnanomolar affinities, and in this example of 0.04 and 0.15 respectively. By comparison, 47-9 was less effective with an IC$_{50}$ value of 0.40 nM (FIG. 6).

EXAMPLE 4-4

Displacement Analysis of [$^{125}$I]Insulin on Insulin Receptor A (IR-A) and B (IR-B) Isoforms by 2D10, 12D5, 13F5 and MA-10

Figure 7:
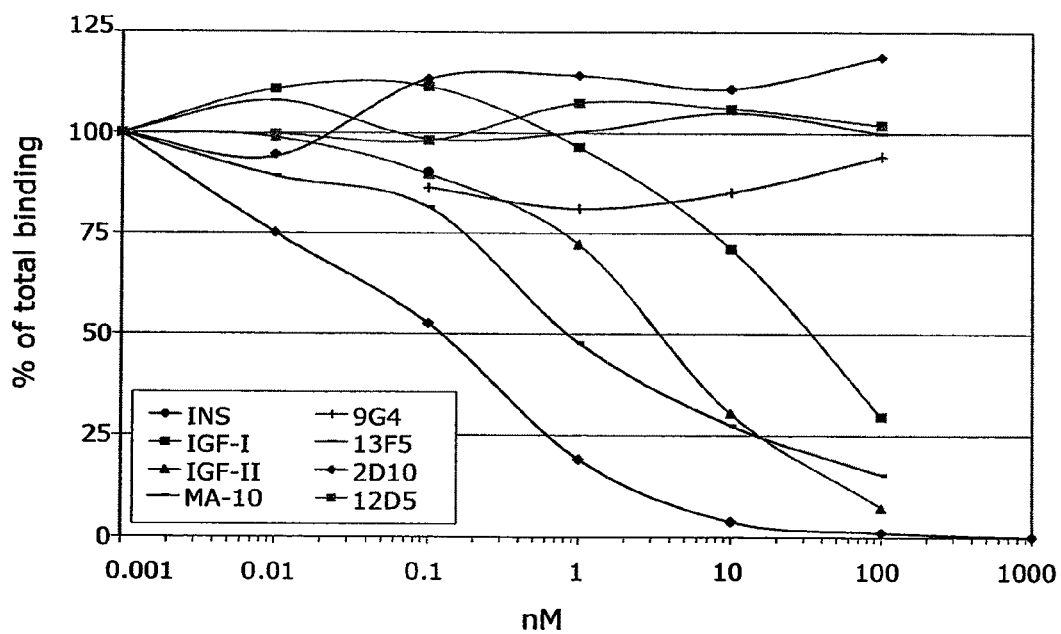
FIG. 7 represents displacement of [$^{125}$I]-INS on intact cells expressing IR-A.
Figure 8:
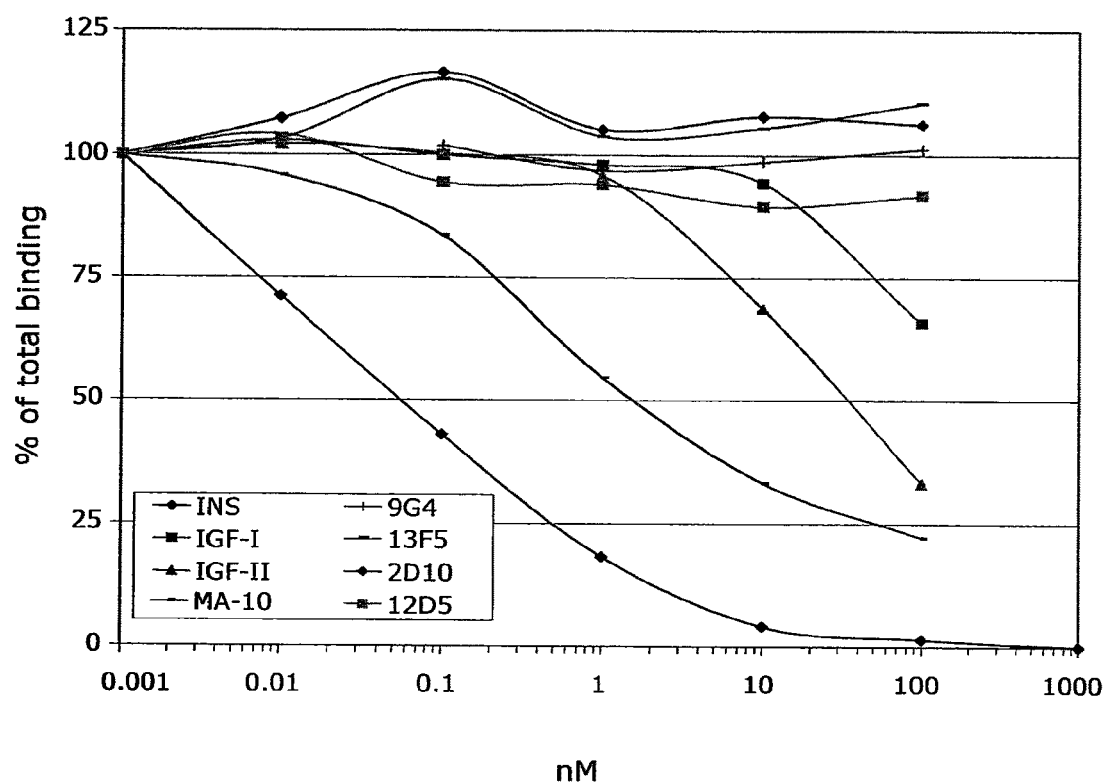
FIG. 8 represents displacement of [$^{125}$I]-INS on intact cells expressing IR-B.

[$^{125}$I]insulin (40,000 cpm) was allowed to bind to R$^-$/IR-A or R$^-$/R-B intact cells for 16 hours at 4° C., in the absence or presence of increasing concentrations of unlabeled ligand (IGF1, IGF2 or insulin) or antibodies (2D10, 12D5, 13F5). Results are plotted as percent of maximal specific binding anr are represented on FIGS. 7 and 8, respectively for IR-A and IR-B.

Neither 2D10, nor 12D5 nor 13F5 displaced insulin, in contrast to the reference antibody MA-10 (IC$_{50}$: 0.90 and 1.5 nM for IR-A (FIG. 7) and IRB (FIG. 8), respectively).

The invention claimed is:

1. An isolated antibody or binding fragment thereof capable of binding to the human insulin-like growth factor I receptor (IGF-IR), wherein the antibody or binding fragment thereof comprises a light chain and a heavy chain, wherein the light chain comprises the three complementarity determining regions (CDRs) of sequence SEQ ID NO: 13, 14 and 15; and the heavy chain comprises the three CDRs of SEQ ID NO: 16, 17 and 18.

2. The antibody or binding fragment thereof of claim 1, wherein the antibody is called 2D10 and comprises a heavy chain amino acid sequence of SEQ ID NO: 25 and a light chain amino acid sequence of SEQ ID NO: 24.

3. A murine hybridoma capable of secreting the antibody as claimed in claim 1 which has been deposited at the CNCM, Institut Pasteur, Paris, on Mar. 25, 2004 under the number I-3214.

4. An antibody secreted by the hybridoma as claimed in claim 3 or a binding fragment thereof.

5. The antibody or binding fragment thereof of claim 1, wherein the antibody is a chimeric antibody.

6. A composition comprising the antibody or binding fragment thereof as claimed in claim 1 and a pharmaceutically acceptable carrier.

7. A composition comprising the antibody produced by the hybridoma of claim 3 or the binding fragment thereof and a pharmaceutically acceptable carrier.

8. The composition as claimed in claim 6, further comprising a cytotoxic agent, a cytostatic agent, and/or an inhibitor of the tyrosine kinase activity of the receptor for IGF-I and/or for EGF.

* * * * *